US012558410B2

(12) United States Patent
Dallmeier et al.

(10) Patent No.: US 12,558,410 B2
(45) Date of Patent: Feb. 24, 2026

(54) LASSAVIRUS VACCINES

(71) Applicant: KATHOLIEKE UNIVERSITEIT LEUVEN, Leuven (BE)

(72) Inventors: Kai Dallmeier, Kessel-Lo (BE); Viktor Lemmens, Leuven (BE); Johan Neyts, Kessel-Lo (BE); Lorena Sanchez Felipe, Wijgmaal (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 807 days.

(21) Appl. No.: 17/642,795

(22) PCT Filed: Sep. 11, 2020

(86) PCT No.: PCT/EP2020/075541
§ 371 (c)(1),
(2) Date: Mar. 14, 2022

(87) PCT Pub. No.: WO2021/048402
PCT Pub. Date: Mar. 18, 2021

(65) Prior Publication Data
US 2022/0378903 A1      Dec. 1, 2022

(30) Foreign Application Priority Data
Sep. 13, 2019    (EP) ..................................... 19197202

(51) Int. Cl.
*A61K 39/12*          (2006.01)
*A61P 31/14*          (2006.01)
*A61K 39/00*          (2006.01)

(52) U.S. Cl.
CPC .............. *A61K 39/12* (2013.01); *A61P 31/14* (2018.01); *A61K 2039/5254* (2013.01); *A61K 2039/5256* (2013.01)

(58) Field of Classification Search
None
See application file for complete search history.

(56) References Cited

FOREIGN PATENT DOCUMENTS

| EP | 3498850 A1 | 6/2019 | |
|----|------------|--------|--|
| WO | 2005042014 A1 | 5/2005 | |
| WO | WO-2009114207 A2 * | 9/2009 | ............. A61K 39/12 |
| WO | 2014174078 A1 | 10/2014 | |
| WO | 2019018501 A1 | 1/2019 | |

OTHER PUBLICATIONS

International Search Report mailed Jan. 19, 2021 in reference to co-pending European Patent Application No. PCT/EP2020/075541 filed Sep. 11, 2020.

Weniger, et al., "Alternative vaccine delivery methods", Section Three, Vaccines in development and new vaccine strategies, pp. 1201-1231, 2013.
Bredenbeek, et al., "A recombinant Yellow Fever 17D vaccine expressing Lassa virus glycoproteins", Rapid Communication, Virology, vol. 345, pp. 299-304, 2006.
Burri, et al., "Envelope Glycoprotein of Arenaviruses", Viruses, vol. 4, pp. 2162-2181, 2012.
Carrion Jr. et al., "A ML29 reassortant virus protects guinea pigs against a distantly related Nigerian strain of Lassa cirus and can provide sterilizing immunity", Vaccine ScienceDirect, vol. 25, pp. 4093-4102, 2007.
Cicin-Sain, et al., "Vaccination of Mice with Bacteria Carrying a Cloned Herpesvirus Genome Reconstituted in Vivo", Journal of Virology, vol. 77, No. 15, pp. 8249-8255, Aug. 2003.
Darji, et al., "Oral delivery of DNA vaccines using attenuated Salmonella typhimurium as carrier", FEMS Immunology and Medical Microbiology, vol. 27, pp. 341-349, 2000.
Babiuk, et al., "DNA Vaccines Methods and Protocols", Methods in Molecular Medicine, Second Edition, vol. 127, pp. 1-62, 2006.
Hastie, et al., "Structural basis for antibody-mediated neutralization of Lassa virus", Structural Biology, vol. 356, pp. 923-928, Jun. 2, 2017.
Jiang, et al., "Yellow fever 17D-vectored vaccines expressing Lassa virus GP1 and GP2 glycoproteins provide protection against fatal disease in guinea pigs", Vaccine, vol. 29, pp. 1248-1257, 2011.
Muller, et al., "The flavivirus NS1 protein: Molecular and structural biology, immunology, role in pathogenesis and application as a diagnostic biomarker", Antiviral Research, vol. 98, pp. 192-208, 2013.
Nielsen, et al., "Identification of prokaryotic and eukaryotic signal peptides and prediction of their cleavage sites", Short Communications, Protein Engineering, vol. 10, No. 1, pp. 1-6, 1997.
Nowak, et al., "Analayses of the Terminal Sequences of West Nile Structural Proteins and of the in Vitro Translation of these Proteins Allow the Proposal of a Complete Scheme of the Proteolytic Cleavages Involved in Their Synthesis", Virology, vol. 169, pp. 365-376, 1989.
Nunberg, et al., "The Curious Case of Arenavirus Entry, and its Inhibition", Viruses, vol. 4, pp. 83-101, 2012.

* cited by examiner

*Primary Examiner* — Stacy B Chen
(74) *Attorney, Agent, or Firm* — DINSMORE & SHOHL LLP

(57) ABSTRACT

The present invention relates to polynucleotides comprising a sequence of a live, infectious, attenuated Flavivirus wherein a nucleotide sequence encoding at least a part of a arenavirus glycoprotein protein is located at the intergenic region between the E and NS1 gene of said Flavivirus, such that a chimeric virus is expressed, characterised in that the encoded sequence C terminally of the E protein of said Flavivirus and N terminally of the signal peptide of the NS1 protein of said Flavivirus comprises in the following order: —a further signal peptide of a Flavivirus NS1 protein, —an arenavirus Glycoprotein protein lacking the N terminal signal sequence and the GP2 transmembrane domain, —a TM1 and TM2 domain of a flaviviral E protein.

20 Claims, 7 Drawing Sheets
Specification includes a Sequence Listing.

1) PLLAV-YFV17D-LASV-GPC (mutated cleavage site)

2) PLLAV-YFV17D-LASV-GPCcs (cleavage site)

YF17D                    YF17D-LASV-GPC 8 x 10⁴ pfu/ml          1.5 x 10³ pfu/ml TCID50/ml:     1,46 x 10⁶          7,90 x 10⁴

1) PLLAV-YFV17D-LASV-GPC (mutated cleavage site)

2) PLLAV-YFV17D-LASV-GPCcs (cleavage site)

YFV17D                    YFV17D-LASV-GPCcs
                          1,4 x 10³ PFU

αYF                    LAS-GPC                    Merge

LASSAVIRUS VACCINES

CROSS REFERENCES TO RELATED APPLICATIONS

This application is a national-stage application under 35 U.S.C. § 371 of International Application No. PCT/EP2020/075541, filed Sep. 11, 2020, which International Application claims benefit of priority to European Patent Application No. 19197202.5, filed Sep. 13, 2019.

The invention relates to chimeric Flavivirus based vaccines. The invention further relates to vaccines against viruses such as Lassa Virus.

BACKGROUND OF THE INVENTION

Currently, there is no licensed human vaccine approved against Lassa virus (LASV). A number of different vaccine candidates have been generated involving several platform technologies. The most advanced candidates are VSV based LASV (VSV-LASV-GPC), a Mopeia virus (MOPV)/LASV reassortant virus (clone ML29) and a DNA vaccine called INO-4500 (pLASV-GPC). VSV based LASV vaccine candidate consists in a replication-competent VSVs expressing the glycoprotein of LASV. ML29 is a reassortant between Lassa and Mopeia viruses that carries the L-segment of MOPV and the S-segment (nucleoprotein and glycoprotein) from LASV. INO-4500 is a DNA vaccine encoding the LASV-GPC gene from Josiah strain f and it is from Inovio company (pLASV-GPC).

Besides the use of the different approaches mentioned above, also yellow fever virus 17D has been used as vector for Lassa virus glycoprotein (GPC) or its subunits GP1 and GP2 (Bredenbeek et al. (2006) *Virology* 345, 299-304 and Jiang et al. (2011) *Vaccine* 29, 1248-1257)). In these constructs the GP gene (lack of signal peptide, SSP) (or either GP1 or GP2 sequences) were inserted between YF-E/NS1. These constructs have at the C-terminus of the insert fusion sequences derived from YF-E, WNV-E or artificial designed sequences. These constructs need to be transfected in cells and the viruses derived from them are used as vaccines.

The only vaccine that have just started a phase I clinical trial is INO-4500 (pLASV-GPC). This vaccine requires multiple high doses delivered via dermal electroporation in order to achieve full protection and enhance the vaccine immune response. This multi-dose administration regimen will be very challenging to implement in the rural areas of West Africa where LASV is endemic and the main outbreaks have occurred.

Regarding the other candidates, ML29 is classified in risk group 2 by the EU and risk group 3 by US CDC what is an obstacle for further development of this vaccine. VSV-LASV-GPC still requires a cold chain to preserve it which involves high cost and still there are no studies concerning its safety. The approach involving YF17D as vector to express Lassa glycoprotein precursor was not successful in NHP studies (0% survival, marmosets).

In addition, this vaccine candidate showed issues of genetic instability that did not allow to scale-up the technology as required for vaccine production.

SUMMARY OF THE INVENTION

We have used our PLLAV (plasmid-launched live-attenuated vaccine) technology and the live-attenuated yellow fever vaccine strain (YFV-17D) as vector to engineer a transgenic vaccine by inserting LASV-GPC (with a mutation in the cleavage site R246A to keep GP1 and GP2 bound and additional mutations R207C, G360C and E329P) into yellow fever E/NS1 intergenic region as follows: N-terminal (Nt) signal peptide was deleted, first 9 amino acids of NS1 (27 nucleotides) were added Nt of LASV-GPC to allow proper release of LASV-GPC protein, the transmembrane domain was deleted and the ectodomain was fused to the WNV transmembrane domain 1 and 2. The resulting PLLAV-YFV17D-LASV-GPC launches viable live-attenuated viruses expressing functional LASV-GPC and YFV-17D proteins. The PLLAV-YFV17D-LASV-GPC construct can be used directly as vaccine what involves that this vaccine is thermostable. The vaccine induces immune responses against both LASV and YFV after one-single shot. A second similar construct has been generated in which the cleavage site has been restored (R246A mutation was restored to R246R). (Additional information in the attached data)

PLLAV-YFV17D-LASV-GPC is a dual vaccine inducing YFV and Lassa virus specific immunity. PLLAV-YFV17D-LASV-GPC can also be used as stable seed for the production of tissue culture-derived live-attenuated vaccine not only in the PLLAV modality, but also unexpectedly the recombinant YFV17D-LASV-GPC virus appears to be genetically more than that disclosed in prior art by Bredenbeek et al. and Jiang et al. (cited above).

The invention is further summarized in the following statements:

1. A polynucleotide comprising a sequence of a live, infectious, attenuated Flavivirus wherein a nucleotide sequence encoding at least a part of a arenavirus glycoprotein protein is located at the intergenic region between the E and NS1 gene of said Flavivirus, such that a chimeric virus is expressed, characterised in that the encoded sequence C terminally of the E protein of said Flavivirus and N terminally of the signal peptide of the NS1 protein of said Flavivirus comprises in the following order:
   a further signal peptide of a Flavivirus NS1 protein,
   an arenavirus Glycoprotein protein lacking the N terminal signal sequence and the GP2 transmembrane domain,
   a TM1 and TM2 domain of a flaviviral E protein.

2. The polynucleotide according to clause 1, wherein the sequence of the live, infectious, attenuated Flavivirus is Yellow Fever virus, typically the YF17D strain.

3. The polynucleotide according to clause 1, wherein the live, infectious, attenuated Flavivirus backbone is a chimeric backbone of two different flaviviruses.

4. The polynucleotide according to any one of clauses 1 to 3, wherein the arena virus a Mammarena virus.

5. The polynucleotide according to any one of clauses 1 to 4, wherein the arenavirus a Lassa virus.

6. The polynucleotide according to any one of clauses 1 to 3, wherein the Lassa strain is the Josiah strain.

7. The polynucleotide according to any one of clauses 1 to 6, wherein the glycoprotein comprises the R207C, G360C and E329P stabilizing mutations.

8. The polynucleotide according to any one of clauses 1 to 7, wherein the glycoprotein comprises the R246A proteolytic cleavage site.

9. The polynucleotide according to any one of clauses 1 to 8, wherein the nucleotide sequence of the G protein is codon optimised for improved expression in mammalian cells.

10. The polynucleotide according to any one of clauses 1 to 9, wherein the signal peptide of the NS1 protein comprises or consists of the sequence DQGCAINFG [SEQ ID NO: 10].

11. The polynucleotide according to any one of clauses 1 to 10, wherein the TM1 and TM2 domain of a flaviviral E protein are from West Nile virus.

12. The polynucleotide according to any one of clauses 1 to 11, wherein the TM1 domain of a flaviviral E protein has the sequence of SEQ ID: NO 14.

13. The polynucleotide according to any one of clauses 1 to 12, wherein the TM2 domain of a flaviviral E protein has the sequence of SEQ ID NO 15.

14. The polynucleotide according to any one of clauses 1 to 13, wherein the sequence of the chimeric virus at the junction of the NS1 signal sequence and the GP1 domain comprises the sequence of SEQ ID NO:11.

15. The polynucleotide according to any one of clauses 1 to 14, wherein the sequence of the chimeric virus at the junction of the GP2 domain and the TM1 domain comprises the sequence of SEQ ID NO:12.

16. The polynucleotide according to any one of clauses 1 to 14, wherein the sequence of the chimeric virus at the junction of the TM2 domain and NS1 protein comprises the sequence of SEQ ID NO:13.

In preferred embodiments the junctions connecting the flavirus NS1 signal sequence, the Lassavirus G protein, the TM2 protein and the second NS1 signal sequence provide a fingerprint for the encoded proteins. Thus embodiments of encoded sequences can be defined by sequences having the sequence of SEQ ID NO:2 or SEQ ID NO: 4, comprising the sequences with SEQ ID NO: 11, SEQ ID: NO 12 and SEQ ID NO13; and wherein outside SEQ ID NO: 11, SEQ ID: NO 12 and SEQ ID NO13, a number of amino acids may differ from SEQ ID NO:2 or SEQ ID NO:4, e.g. differing up to 20, up to 10, or up to 5 compared to SEQ ID NO:2 or SEQ ID NO: 4, or e.g. having a sequence identity of at least 95%, 96%, 97%, 98% or 99% with SEQ ID NO:2 or SEQ ID NO:4.

17. The polynucleotide according to any one of the clauses 1 to 16, which is a bacterial artificial chromosome.

18. A polynucleotide in accordance to any one of clauses 1 to 17, for use as a medicament.

19. The polynucleotide for use as a medicament in accordance with clause 18, wherein the medicament is a vaccine.

20. A polynucleotide sequence in accordance to any one of clauses 1 to 17, for use in the vaccination against an arenavirus infection.

21. A chimeric live, infectious, attenuated Flavivirus wherein at least a part of an arenavirus Glycoprotein is located between the E and NS1 protein of said Flavivirus, such that C terminally of the E protein and N terminally of the signal peptide of the NS1 protein the virus comprises in the following order:

a further signal peptide of a Flavivirus NS1 protein,
an arenavirus Glycoprotein protein lacking the N terminal signal sequence and the GP2 transmembrane domain,
a TM1 and TM2 domain of a flaviviral E protein.

22. The chimeric Flavivirus according to clause 21, wherein the Flavivirus is YFV.

23. The chimeric Flavivirus according to clause 21 or 22, wherein the arenavirus is Lassa virus.

24. A chimeric virus in accordance to any one of clauses 21 to 23, for use as a medicament.

25. A chimeric virus in accordance to any one of clauses 21 to 24, for use in the prevention of an Arenaviral infection.

26. A chimeric virus encoded by a nucleotide in accordance to any one of clauses 21 to 23, for use in the prevention of an Arenaviral infection and in the prevention of the Flavivirus.

27. A method of preparing a vaccine against an arenaviral infection, comprising the steps of:

providing a BAC which comprises:
an inducible bacterial ori sequence for amplification of said BAC to more than 10 copies per bacterial cell, and
a viral expression cassette comprising a cDNA of a arenaviral-flaviviral chimeric virus according to any one of clauses 1 to 16, and comprising cis-regulatory elements for transcription of said viral cDNA in mammalian cells and for processing of the transcribed RNA into infectious RNA virus,
transfecting mammalian cells with the BAC of step a) and passaging the infected cells,
validating replicated virus of the transfected cells of step b) for virulence and the capacity of generating antibodies and inducing protection against said arenaviral infection,
cloning the virus validated in step c into a vector, and
formulating the vector into a vaccine formulation.

28. The method according to clause 27, wherein the Flavivirus is yellow fever virus.

29. The method according to clause 27 or 28, wherein the arenavirus is Lassa virus.

30. The method according to any one of clauses 27 to 29, wherein the vector is a BAC, which comprises an inducible bacterial ori sequence for amplification of said BAC to more than 10 copies per bacterial cell.

BRIEF DESCRIPTION OF THE DRAWINGS

FIG. 2A) Plaque phenotype of YFV17D-LASV-GPC compared to YFV17D. FIG. 2B) Virus stability: RT-PCR analysis of the virus samples harvested during serial passaging (in BHK-21J and VeroE6) of the YFV17D-LASV-GPC virus. C+, control positive PLLAV-YFV17D-LASV-GPC;-RT: RT-PCR reaction without reverse transcriptase; RNA: RT-PCR reaction with the virus RNA.

FIG. 4A) Representative IFN-γ ELISPOT wells after 48 hours of stimulation of splenocytes with the indicated antigen. FIG. 4B) Spots per six hundred thousand splenocytes in IFN-γ ELISPOT after 48 hours of stimulation with the indicated antigen. For each mouse, samples were analyzed in duplicates and values are normalized by subtracting the number of spots in control wells (ovalbumin stimulated).

FIG. 5A) Plaque phenotype of YFV17D-LASV-GPCcs compared to YFV17D. FIG. 5B) Co-expression of LASV-GPC and YFV antigens detected by immunofluorescence of BHK21J cells infected with supernatant of cells transfected with PLLAV-YFV17D-LASV-GPCcs.Cells were fixed 48h post-infection and stained for LAV-GPC (red) and YFV (green).

FIG. 6A) Schematic vaccination schedule. AG129 mice were vaccinated subcutaneous (SC) with YFV17D-LASV-GPCcs (250 PFU). FIG. 6B) Analysis of cellular immunity in vaccinated AG129 mice. Representative IFN-gamma ELISPOT wells after 48 hours splenocyte stimulation with the indicated antigen. Spots per six hundred thousand splenocytes in IFN-gamma ELISPOT after 48 hours of stimulation with the indicated antigen. For each mouse, samples were analyzed in duplicates and values are normalized by subtracting the number of spots in control wells (ovalbumin peptide stimulated).

DETAILED DESCRIPTION

Figure 1A:
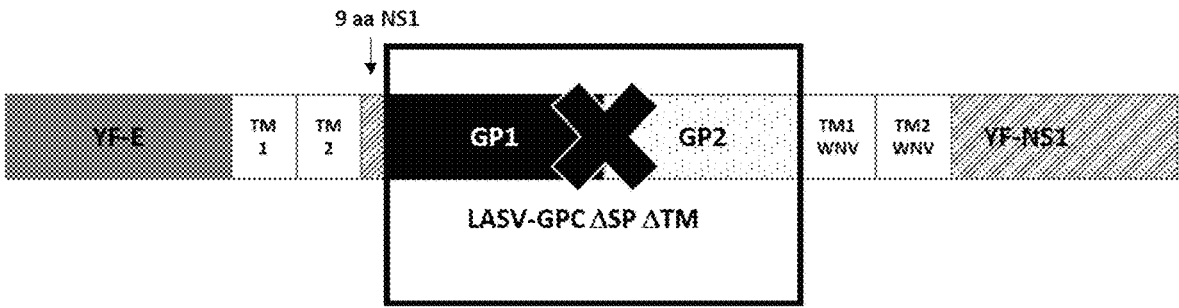
FIGS. 1A-1B: Schematic representation of 1) PLLAV-YFV17D-LASV-GPC (FIG. 1A) and 2) PLLAV-YFV17D-LASV-GPCs (FIG. 1B).
Figure 1A:
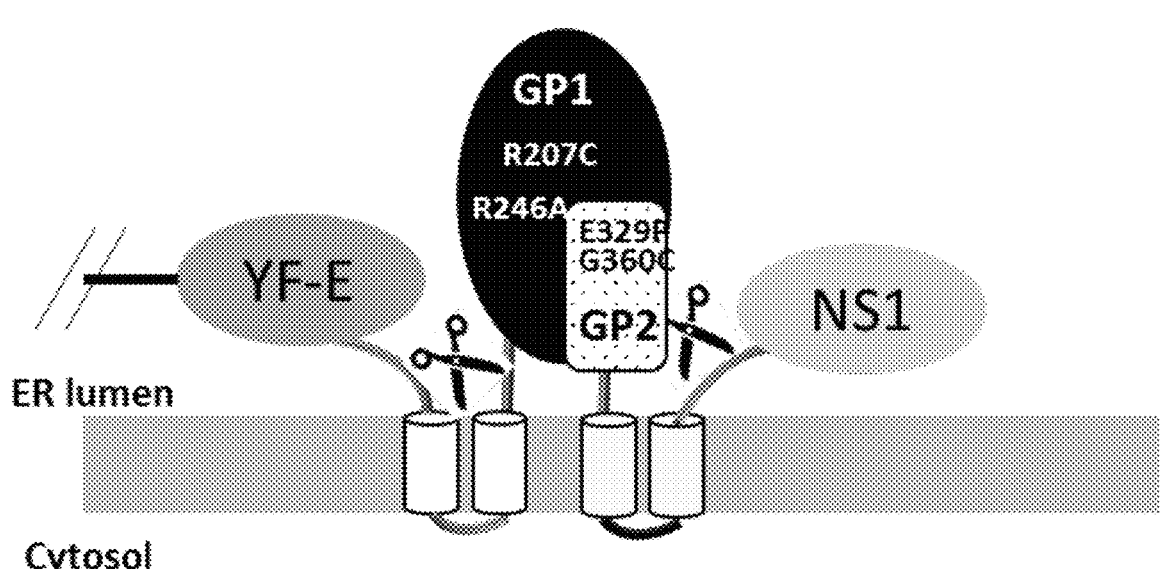
Figure 1B:
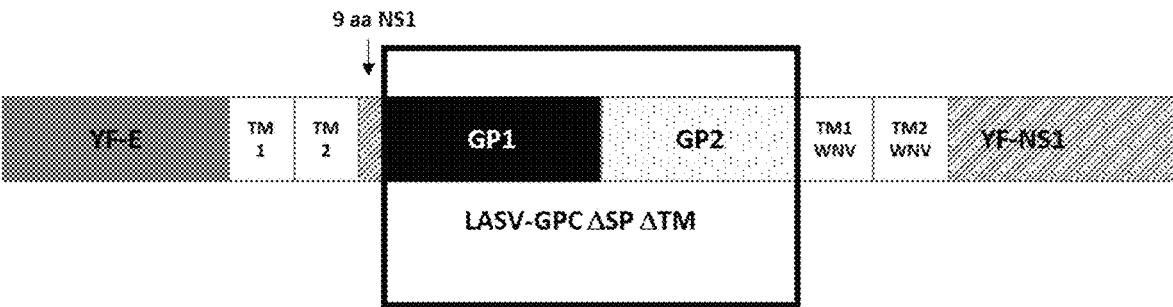
Figure 1B:
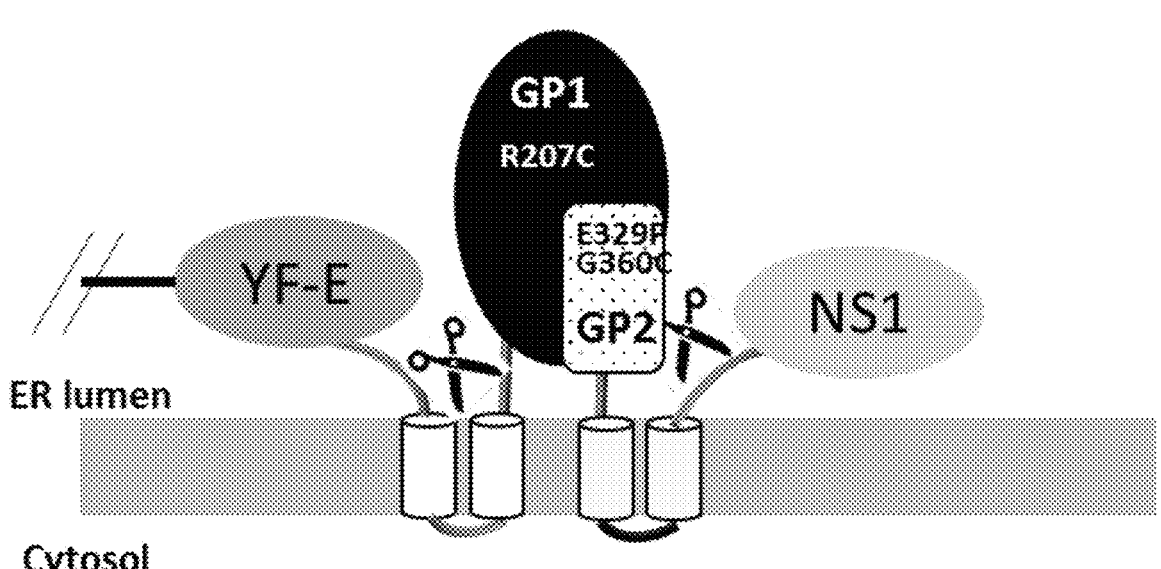

The present invention is exemplified for Yellow Fever virus, but is also applicable using other viral backbones of Flavivirus species such, but not limited to, Japanese Encephalitis, Dengue, Murray Valley Encephalitis (MVE), St. Louis Encephalitis (SLE), West Nile (WN), Tick-borne Encephalitis (TBE), Russian Spring-Summer Encephalitis (RSSE), Kunjin virus, Powassan virus, Kyasanur Forest Disease virus, Zika virus, Usutu virus, Wesselsbron and Omsk Hemorrhagic Fever virus.

The invention is further applicable to Flaviviridae, which comprises the genus *Flavivirus* but also the genera, *Pegivirus, Hepacivirus* and *Pestivirus.*

The genus *Hepacivirus* comprises e.g. Hepacivirus C (hepatitis C virus) and Hepacivirus B (GB virus B)

The genus *Pegivirus* comprises e.g. Pegivirus A (GB virus A), Pegivirus C (GB virus C), and Pegivirus B (GB virus D).

The genus *Pestivirus* comprises e.g. Bovine virus diarrhea virus 1 and Classical swine fever virus (previously hog cholera virus).

The Flavivirus which is used as backbone can itself by a chimeric virus composed of parts of different Flavivirus.

For example the C and NS1-5 region are from Yellow Fever and the prME region is of Japanese encephalitis or of Zika virus.

The present invention is exemplified for the G protein of Lassa virus but is also applicable to G proteins of other arenaviruses.

The present invention relates to nucleotide sequence and encoded proteins wherein within the RNA or copy DNA (cDNA) of a flavivirus a glycoprotein of an arenavirus is inserted Glycoproteins of Arenavirus are discussed in Burr et al. (2012) Viruses 4, 2162-2181 and in Nurnberg & Yorke (2012) Viruses 4, 83-101. Arenaviruses are comprised of two RNA genome segments and four proteins, the polymerase L, the envelope glycoprotein GP (also referred to in the present invention as G protein or GPC), the matrix protein Z, and the nucleoprotein NP.

In the arenavirus life-cycle the biosynthesis and maturation of the GP precursor (GPC) is performed by cellular signal peptidases and the cellular enzyme Subtilisin Kexin Isozyme-1 (SKI-1)/Site-1 Protease (S1P) yielding a tripartite mature GP complex formed by GP1/GP2 and a stable signal peptide (SSP).

Based on serological, genetic and geographical data, Mammarenavirus arenaviruses are divided into two major subgroups: the Old World (OW) and the New World (NW) complex. The Old World lineage consists of the prototypic LCMV and other viruses endemic to the African continent, including Lassa (LASV), Mopeia (MOPV), Ippy, and Mobala (MOBV) viruses.

The larger New World complex is further divided into three clades, A, B and C. Clade B is the most important in term of human disease, since it contains the major viruses causing hemorrhagic fevers (HF) in South America, i.e. Junin (JUNV), Machupo (MACV), Guanarito (GTOV) and Sabia (SABV) viruses but also other non-pathogenic viruses, like Tacaribe (TCRV) and Amapari virus (AMPV).

The present invention envisages chimeric constructs based on G proteins of any of the above groups, subgroups or species are used. Preferred embodiment are constructs based on G proteins of the LASV inserted within a flavivirus RNA or cDNA.

The present invention envisages chimeric constructs based on G proteins of Reptarenaviruses or Hartmaniviruses are used.

The present invention is exemplified with G protein of Lassa virus strain Josiah. This sequence of this protein is accessible for example as UniProtKB P08669 database entry or as NCBI NP_694870.1 database entry.

In alternative embodiment the arenavirus envisaged is a virus wherein the protein sequence of the G protein has a sequence identity of at least 70, at least 80, at least 90, at least 95, or least 99% identity with the G protein of Lassa virus strain Josiah, as disclosed in the above cited database entries.

The constructs of the present invention allow a proper presentation of the encoded insert into the ER lumen and proteolytic processing. As exemplified by Lassa G protein, the encoded protein by the insert lacks the N terminal signal sequence and a GP2 transmembrane domain. To preserve the required topology two transmembrane domains of e.g. WNV are fused c terminally to the glycoprotein sequence. Based on this principle any immunogenic protein can be presented via the vector of the present invention that the protein lacks an N terminal membrane targeted domain and contains at the C terminus a targeting membrane followed by a cytoplasmic sequence to allow the connection with the transmembrane membrane preceding the NS1 protein.

The invention is now further described for embodiments wherein a Flavivirus is used as backbone and a G protein of Lassa virus as insert.

The high sequence identity between G proteins of different arenavirus presents no problems to the skilled person to identify in related sequences the sequence elements corresponding to those present in Lassa virus G protein.

Flaviviruses have a positive single-strand RNA genome of approximately 11,000 nucleotides in length. The genome contains a 5' untranslated region (UTR), a long open-reading frame (ORF), and a 3' UTR. The ORF encodes three structural (capsid [C], precursor membrane [prM], and envelope [E]) and seven nonstructural (NS1, NS2A, NS2B, NS3, NS4A, NS4B, and NS5) proteins. Along with genomic RNA, the structural proteins form viral particles. The nonstructural proteins participate in viral polyprotein processing, replication, virion assembly, and evasion of host immune response. The signal peptide at the C terminus of the C protein (C-signal peptide; also called C-anchor domain) regulates Flavivirus packaging through coordination of sequential cleavages at the N terminus (by viral NS2B/NS3 protease in the cytoplasm) and C terminus (by host signalase in the endoplasmic reticulum [ER] lumen) of the signal peptide sequence.

The positive-sense single-stranded genome is translated into a single polyprotein that is co- and post translationally cleaved by viral and host proteins into three structural [Capsid (C), premembrane (prM), envelope (E)], and seven non-structural (NS1, NS2A, NS2B, NS3, NS4A, NS4B, NS5) proteins. The structural proteins are responsible for forming the (spherical) structure of the virion, initiating virion adhesion, internalization and viral RNA release into cells, thereby initiating the virus life cycle. The non-structural proteins on the other hand are responsible for viral replication, modulation and evasion of immune responses in infected cells, and the transmission of viruses to mosquitoes. The intra- and inter-molecular interactions between the structural and non-structural proteins play key roles in the virus infection and pathogenesis.

The E protein comprises at its C terminal end two transmembrane sequences, indicated as TM1 and TM2.

NS1 is translocated into the lumen of the ER via a signal sequence corresponding to the final 24 amino acids of E and is released from E at its amino terminus via cleavage by the ER resident host signal peptidase (Nowak et al. (1989) *Virology* 169, 365-376). The NS1 comprises at its C terminal a 8-9 amino acids signal sequence which contains a recognition site for a protease (Muller & Young (2013) *Antiviral Res.* 98, 192-208)

The constructs of the present invention are chimeric viruses wherein a Lassa G protein is inserted at the boundary between the E and NS1 protein. However additional sequence elements are provided N terminally and C terminally of the G protein insert.

The invention relates to polynucleotide comprising a sequence of a live, infectious, attenuated Flavivirus wherein a nucleotide sequence encoding at least a part of a arenavirus G protein is inserted at the intergenic region between the E and NS1 gene of said Flavivirus, such that a chimeric virus is expressed, characterised in that the encoded sequence C terminally of the E protein of said Flavivirus and N terminal the NS1 protein of said Flavivirus comprises in the following order:

a sequence element allowing the proteolytic processing of the G protein from the E protein by a signal peptidase.

a G protein lacking its signal peptide and a GP2 transmembrane protein, and a two TM domains of the E protein of a flavivrus To allow proteolytic processing of the arenavirus G protein from the Flavivirus E protein at its aminoterminal end and allow proteolytic processing of the arenavirus G protein from the Flavivirus NS1 protein at its C terminal, sequence elements are provided which are substrates for a signal peptidase. These can vary in length and in sequence, and can be as short as one amino acid as shown in Jang et al. cited above. A discussion on suitable recognition sites for signalling proteases is found in Nielsen et al. (1997) *Protein Eng.* 10, 1-6.

Typically, at the C terminus of the G protein, the signal peptide at the N terminus of the NS1 protein will be used (or a fragment which allows proteolytic processing). Typically, at the N terminus of the G protein, the same signal peptide (or fragment) of the NS1 protein of the Flavivirus backbone is introduced.

The invention equally relates to polynucleotides comprising a sequence of a live, infectious, attenuated Flavivirus. Herein a nucleotide sequence encoding at least a part of an arenavirus G protein is inserted at the intergenic region between the E and NS1 gene of said Flavivirus. Additional sequences are provided such that when the chimeric virus is expressed such that the encoded sequence from the C terminally of the E protein to the N terminus of the signal peptide of the NS1 protein comprises in the following order:

a further signal peptide (or cleavable fragment thereof) of a Flavivirus NS1 gene, C terminal to the E protein and N terminal to the NS1 protein.

a arenavirus G protein lacking a functional signal peptide and a transmembrane sequence of the GP2 domain. This G protein is C terminally positioned from a NS1 signal peptide. C terminally of the G protein is the sequence of a Flavivirus TM1 and TM2 transmembrane domain of a Flavivirus. C terminally of these TM sequence follows the NS1 protein, including its native signal peptide sequence.

Thus, the G protein and the TM domains are flanked at N terminus and C terminus by an NS1 sequence. In the embodiments disclosed in the examples the protein and DNA sequence of both NS1 are identical.

In typical embodiments both NS1 signal sequences have the sequence DQGCAINFG [SEQ ID NO:10].

The constructs of the present invention did not show recombination due to the presence of this repetitive sequence. Sequence modifications can be introduced or NS1 sequences from different Flavivirus can be used to avoid presence of identical sequences, as long as the encoded peptide remains a target from the protease which processes these NS1 N-terminal signal sequences.

In typical embodiments, as disclosed in the examples, the G protein is of Lassa virus, preferably of the Josiah strain of Lassa virus.

To facilitate the production of virus in the mammalian hosts, the nucleotide sequence of the G protein is codon optimized.

It is submitted that minor sequence modifications in the G protein and in the C terminal tail can be introduced without loss of function of these sequence elements. For example, amino acids substitutions wherein hydrophobic side chains are preserved in the transmembrane domain, or truncated versions of the cytoplasmic domain with sufficient length to allow proper localisation of the transmembrane domains at the N terminus and C terminus of the cytoplasmatic domain.

It has been found that the presence of a functional signal peptide of the G protein results in a negative selective pressure whereby a part of the G protein comprising its signal peptide is deleted or mutated. Thus the constructs of the present invention typically contain a defective G protein signal by partial or complete removal of this sequence or by the introduction of mutations which render the signal protein non-functional.

The TM domains which are located C terminally of the G protein and N terminally of the NS1 is generally of a Flavivirus, typically from the E protein, and more typical a TM domains of an E protein. In preferred embodiments these TM domains of an E protein are from a different Flavivirus than the virus forming the backbone. The examples of present invention describe the TM1 and TM2 domain of the E protein of the West Nile virus. These domain have the sequence

```
                                    [SEQ ID NO: 14]
        GGMSWITQGLLGALLLWMGINARD
        and

[SEQ ID NO: 15]
        RSIAMTFLAVGGVLLFLSVNVHA.
```

In the examples section below and in the schematic representation all sequence elements form a continuous sequence without any intervening sequence elements. It is submitted that in between these sequence elements, additional amino acids may be present as long as the localisation of the protein at either the ER lumen or cytosol is not disturbed and proteolytic processing is maintained.

The above described nucleotide sequence can be that of the virus itself or can refer to a sequence in a vector. A suitable vector for cloning Flavivirus and chimeric version are, amongst other technologies, Bacterial Artificial Chromosomes, as described in more detail below.

The methods and compounds of the present invention have medicinal application, whereby the virus or a vector encoding the virus can be used to vaccinate against the arenavirus which contains the G protein that was cloned in the Flavivirus. In addition, the proteins from the Flavivirus equally provide protection such that the compounds of the present invention can be used to vaccinate against a Flavivirus and an arenavirus using a single virus or DNA vaccine.

The use of Bacterial Artificial Chromosomes, and especially the use of inducible BACS as disclosed by the present inventors in WO2014174078, is particularly suitable for high yield, high quality amplification of cDNA of RNA viruses such as chimeric constructs of the present invention.

A BAC as described in this publication BAC comprises:

an inducible bacterial ori sequence for amplification of said BAC to more than 10 copies per bacterial cell, and a viral expression cassette comprising a cDNA of an the RNA virus genome and comprising cis-regulatory elements for transcription of said viral cDNA in mammalian cells and for processing of the transcribed RNA into infectious RNA virus.

As is the case in the present invention the RNA virus genome is a chimeric viral cDNA construct of an RNA virus genome and an arenavirus G protein.

In these BACS, the viral expression cassette comprises a cDNA of a positive-strand RNA virus genome, an typically a RNA polymerase driven promoter preceding the 5' end of said cDNA for initiating the transcription of said cDNA, and an element for RNA self-cleaving following the 3' end of said cDNA for cleaving the RNA transcript of said viral cDNA at a set position.

The BAC may further comprise a yeast autonomously replicating sequence for shuttling to and maintaining said bacterial artificial chromosome in yeast. An example of a yeast ori sequence is the 2μ plasmid origin or the ARS1 (autonomously replicating sequence 1) or functionally homologous derivatives thereof.

The RNA polymerase driven promoter of this first aspect of the invention can be an RNA polymerase II promoter, such as Cytomegalovirus Immediate Early (CMV-IE) promoter, or the Simian virus 40 promoter or functionally homologous derivatives thereof.

The RNA polymerase driven promoter can equally be an RNA polymerase I or III promoter.

The BAC may also comprise an element for RNA self-cleaving such as the cDNA of the genomic ribozyme of hepatitis delta virus or functionally homologous RNA elements.

The formulation of DNA into a vaccine preparation is known in the art and is described in detail in for example chapter 6 to 10 of "DNA Vaccines" Methods in Molecular Medicine Vol 127, (2006) Springer Saltzman, Shen and Brandsma (Eds.) Humana Press. Totoma, N.J. and in chapter 61 Alternative vaccine delivery methods, P 1200-1231, of Vaccines (6th Edition) (2013) (Plotkin et al. Eds.). Details on acceptable carrier, diluents, excipient and adjuvant suitable in the preparation of DNA vaccines can also be found in WO2005042014, as indicated below.

"Acceptable carrier, diluent or excipient" refers to an additional substance that is acceptable for use in human and/or veterinary medicine, with particular regard to immunotherapy.

By way of example, an acceptable carrier, diluent or excipient may be a solid or liquid filler, diluent or encapsulating substance that may be safely used in systemic or topic administration. Depending upon the particular route of administration, a variety of carriers, well known in the art may be used. These carriers may be selected from a group including sugars, starches, cellulose and its derivatives, malt, gelatine, talc, calcium sulphate and carbonates, vegetable oils, synthetic oils, polyols, alginic acid, phosphate buffered solutions, emulsifiers, isotonic saline and salts such as mineral acid salts including hydrochlorides, bromides and sulphates, organic acids such as acetates, propionates and malonates and pyrogen-free water.

A useful reference describing pharmaceutically acceptable carriers, diluents and excipients is Remington's Pharmaceutical Sciences (Mack Publishing Co. N. J. USA, 2(091) which is incorporated herein by reference.

Any safe route of administration may be employed for providing a patient with the DNA vaccine. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intramuscular and subcutaneous injection may be appropriate, for example, for administration of immunotherapeutic compositions, proteinaceous vaccines and nucleic acid vaccines. It is also contemplated that microparticle bombardment or electroporation may be particularly useful for delivery of nucleic acid vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

DNA vaccines suitable for oral or parenteral administration may be presented as discrete units such as capsules, sachets or tablets each containing a pre-determined amount of plasmid DNA, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the DNA plasmids with liquid carriers or finely divided solid carriers or both, and then, if necessary, shaping the product into the desired presentation.

The above compositions may be administered in a manner compatible with the dosage formulation, and in such amount as is effective. The dose administered to a patient, should be sufficient to effect a beneficial response in a patient over an appropriate period of time. The quantity of agent (s) to be administered may depend on the subject to be treated inclusive of the age, sex, weight and general health condition thereof, factors that will depend on the judgement of the practitioner.

Furthermore DNA vaccine may be delivered by bacterial transduction as using live-attenuated strain of Salmonella transformed with said DNA plasmids as exemplified by Darji et al. (2000) *FEMS Immunol Med Microbiol* 27, 341-349 and Cicin-Sain et al. (2003) *J Virol* 77, 8249-8255 given as reference.

Typically the DNA vaccines are used for prophylactic or therapeutic immunisation of humans, but can for certain viruses also be applied on vertebrate animals (typically mammals, birds and fish) including domestic animals such as livestock and companion animals. The vaccination is envisaged of animals which are a live reservoir of viruses (zoonosis) such as monkeys, dogs, mice, rats, birds and bats.

In certain embodiments vaccines may include an adjuvant, i.e. one or more substances that enhances the immunogenicity and/or efficacy of a vaccine composition However, life vaccines may eventually be harmed by adjuvants that may stimulate innate immune response independent of viral replication. Non-limiting examples of suitable adjuvants include squalane and squalene (or other oils of animal origin); block copolymers; detergents such as Tween-80; Quill A, mineral oils such as Drakeol or Marcol, vegetable oils such as peanut oil; Corynebacterium-derived adjuvants such as Corynebacterium parvum; Propionibacterium-derived adjuvants such as Propionibacterium acne; Mycobacterium bovis (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOMt) and ISCOMATRIX (B) adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

EXAMPLES

Example 1 YFV17D/Lassa Constructs

The Lassa glycoprotein precursor (LASV-GPC) from Josiah strain was inserted between YF-E/NS1 to generate two constructs as follows (FIG. 1):

1) PLLAV-YFV17D-LASV-GPC: Lassa glycoprotein with the N-terminal signal peptide sequence (SSP) and the GP2 transmembrane domain (TM) deleted. The LASV glycoprotein cleavage site was mutated (R246A) to keep the precursor GPC (GP1 and GP2 linked). These point mutations R207C and G360C (bind GP1 and GP2 covalently) and E329P (described in Hastie et al (2017) *Science* 356, 923-928) were introduce to improve stability. This Lassa-GPC with the mutations was fused to the transmembrane domains of WNV (TM1 and TM2) to keep the polyprotein topology required to replicate YFV17D and allow the proper expression of LASV-GPC. In addition, the sequence that codified for the first 9 amino acids of YF-NS1 was introduced before LASV-GPC sequence to allow the correct processing of the antigen.

2) PLLAV-YFV17D-LASV-GPCcs: Similar construct to the one described above but, in this construct, the cleavage site was restored (R246A mutation was restored to R246R). The rest of the mutations were similar, mutations R207C and G360C (bind GP1 and GP2 covalently) and E329P (described in Hastie et al. (2017) *Science* 356, 923-928) were introduced to improve stability.

Example 2 Construct #1 PLLAV-YFV17D-LASV-GPC

Figure 2A:
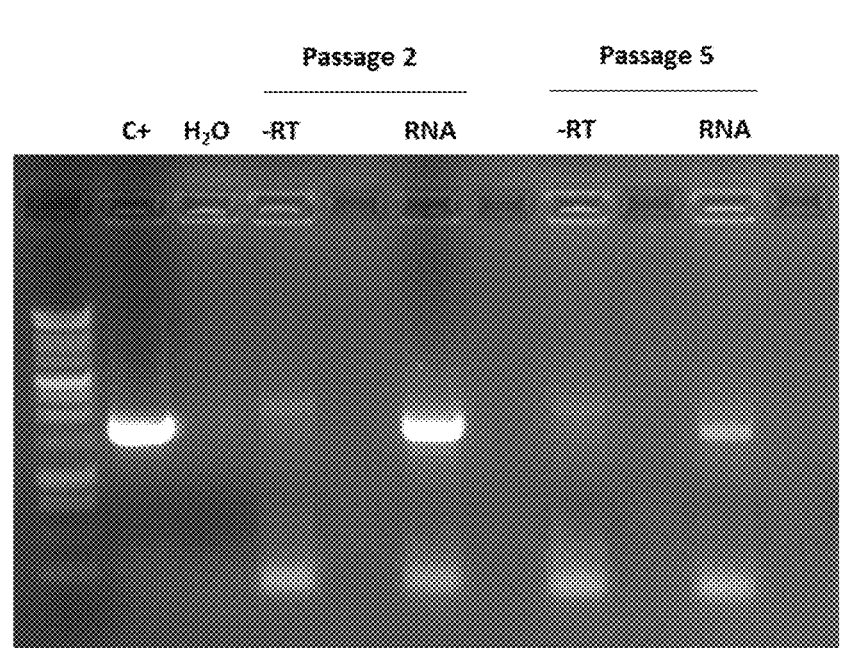
FIGS. 2A-2B.

PLLAV-YFV17D-LASV-GPC was transfected into BHK21J cells and typical CPE was observed as well as the virus supernatant harvested from them formed markedly smaller plaques compared to the plaque phenotype of YFV17D (FIG. 2A). Therefore, the resulting transgenic virus (YFV17D-LASV-GPC) is further attenuated, and virus yields were at least 10-fold less compared to YFV17D.

Figure 2B:
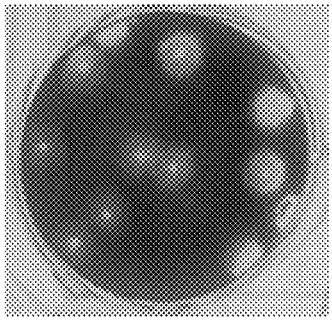
Figure 2B:
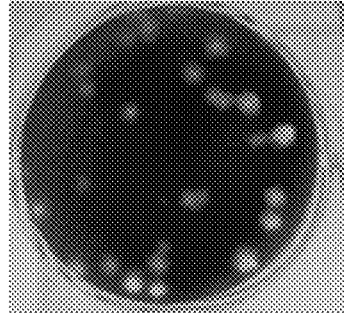

The stability of PLLAV-YFV17D-LASV-GPC was determined by performing RT-PCR to detect the transgene insert in virus samples that were harvested during serial passage of the YFV17D-LASV-GPC (FIG. 2B). Sequencing of the RT-PCR products showed that LASV-GPC insert with no mutations can be detected at least until passage 5 in BHK21J cells.

Example 3 Immunogenicity of PLLAV-YFV17D-LASV-GPC in AG129 Mice

Figure 3:
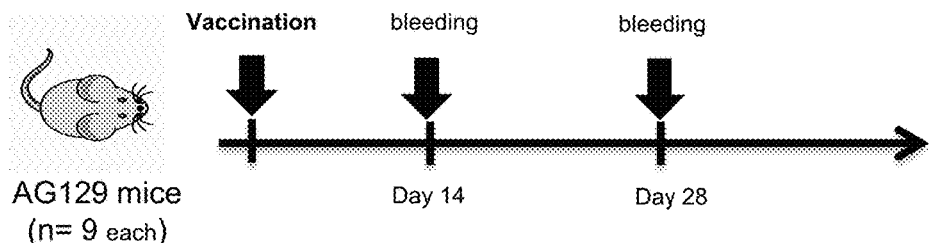
FIG. 3: Schematic vaccination schedule. AG129 mice were vaccinated with PLLAV-YFV17D-LASV-GPC (25 ug, i.p.) or YFV17D-LASV-GPC (375 PFU).
Figure 4A:
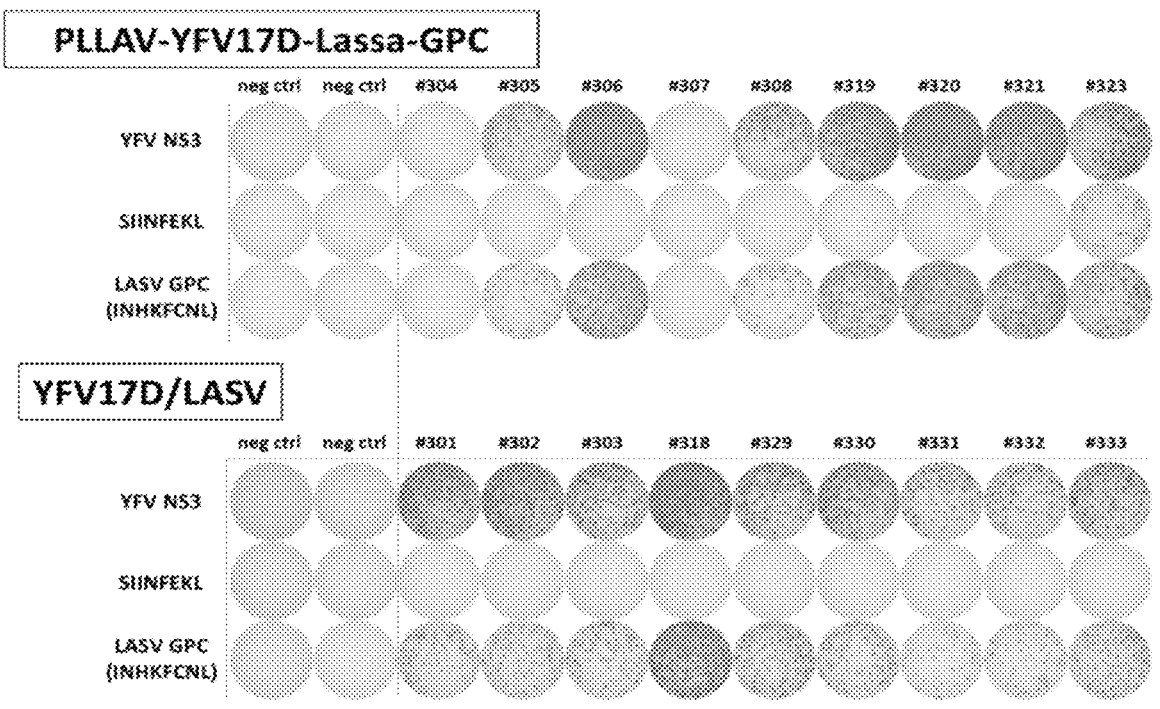
FIGS. 4A-4B: Analysis of cellular immunity in vaccinated AG129 mice.
Figure 4B:
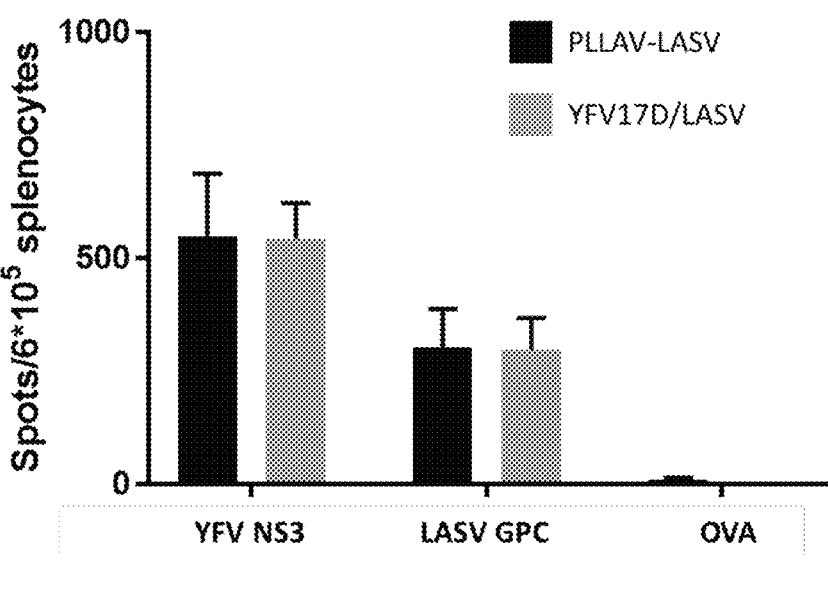

The immunogenicity of PLLAV-YFV17D-LASV-GPC and the derived live-attenuated virus (LAV) was assessed in vivo in AG129 mice. Animals (n=9/group) were vaccinated with either 25 µg of PLLAV-YFV17D-LASV-GPC or 375 PFU of YFV17D-LASV-GPC (FIG. 3). The YFV- and LASV-specific antibody responses were quantified by indirect immunofluorescence assay (IIFA) and the cell mediated immune response was quantified by ELISPOT (FIG. 4).

Vaccinated mice were monitored daily for morbidity/mortality and blood was sampled for serological analysis at baseline and with two-week intervals. The vaccine was safe as no adverse effects were observed in any of the vaccinated mice. Some animals (4 of the 9 mice) were boosted two weeks after first inoculation with the PLLAV or LAV YFV17D-LASV-GPC using same dose and route than in the first vaccination (FIG. 3).

The immunogenicity analysis for YFV17D-LASV-GPC (PLLAV or LAV) revealed that at 14 days post vaccination there were specific antibodies against LASV in 3 and 1 mice vaccinated with PLLAV or LAV respectively. Of note, for LASV it is currently thought that the CD8+ T-cell response is the main determinant responsible for providing protection against LASV infection. Therefore, the T cells responses were analyzed in both groups at 4 months post vaccination. This analysis showed that there was T cells responses against LASV and YFV in all the mice vaccinated with YFV17D-LASV-GPC (LAV) and in 7 out of 9 after vaccination with the PLLAV version (FIG. 4). These T cell responses can hence be considered to confer immunity and protection against LASV infection.

Example 4 Construct #2 PLLAV-YFV17D-LASV-GPCcs (Cleavage Site)

Figure 5A:
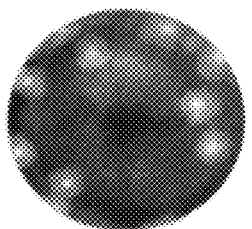
FIGS. 5A-5B.
Figure 5A:
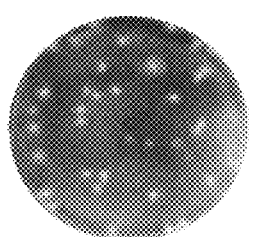

A second construct, similar to the above described, was generated. In this PLLAV-YFV17D-LASV-GPCcs in which the natural cleavage site between GP1 and GP2 was restored. This construct was transfected in BHK21J cells and typical CPE was observed as well as the virus supernatant harvested from them formed markedly smaller plaques compared to the plaque phenotype of YFV17D (FIG. 5A). Therefore, similar to the previous YFV17D/LASV construct, the resulting transgenic virus (YFV17D-LASV-GPC) is further attenuated, and virus yields were at least 10-fold less compared to YFV17D.

Figure 5B:
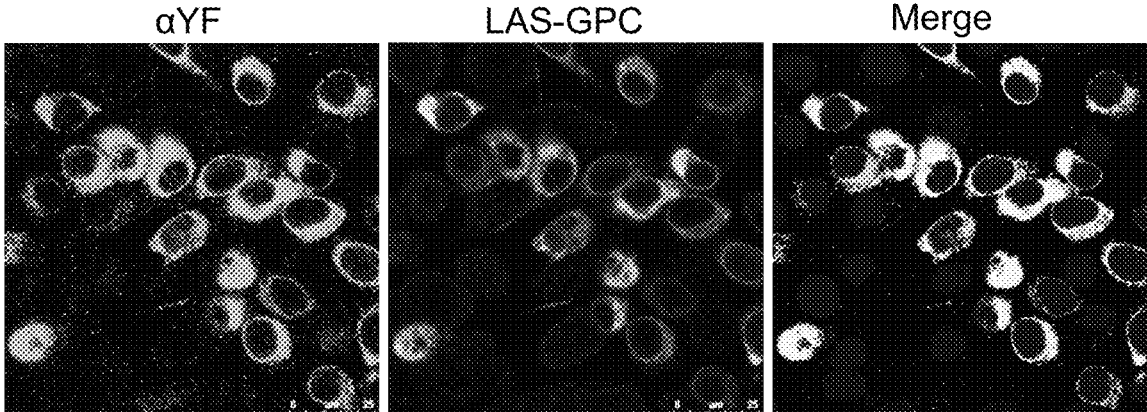

Co-expression of LASV-GPC along with the YFV polyprotein could be confirmed (FIG. 5B) indicating proper expression and folding of LASV-GPC.

Figures 6A, 6B:
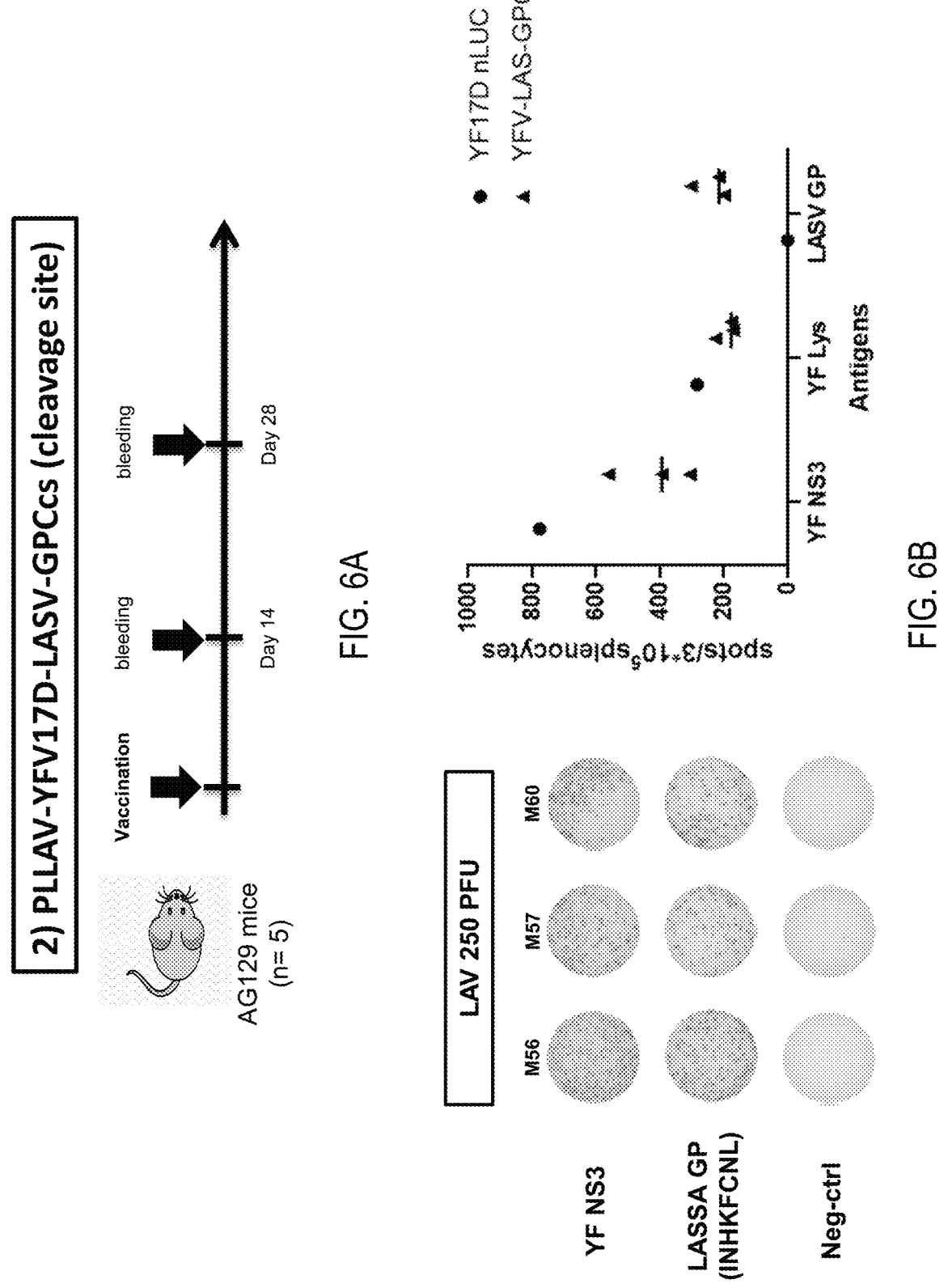
FIGS. 6A-6B.

To assess the immunogenicity of this construct, AG129 mice were vaccinated subcutaneously (s.c.) with YFV17D-LASV-GPCcs (LAV) and the T-cell responses were determined at 28 days post-vaccination (FIG. 6). The analysis show that there was strong specific T cells responses against both, LASV and YFV. These results suggests that the vaccine can work as a bivalent vaccine against both viruses, LASV and YFV. The vaccine was safe as no adverse effects were observed in any of the vaccinated mice.

---

```
                        SEQUENCES DEPICTED IN THE APPLICATION
```

---

```
construct #1: PLLAV-YFV17D-LASV-GPC cleavage
(signal peptide deleted, transmembrane domain g p2deleted, cleavage
sitemutated(r256a) and mutations r207c ,e329p and g360c)

-end YF-E (amino acids 1-40)

-first 27 nucleotide (9 amino acids) of SNS1 (amino acids 41-49) bold
underlined -lasv-gp1 domain [without signal peptide and with mutation tgt
(r207c)] (amino acids 50-250) (amino acids 50-250)

-cleavage site mutated gcaagattgcta(r256a) [SEQ ID NO: 16] (amino
acids 247-250)

-lasv-p2 [without tm and mutations cca(e329p), tgt(g360c)] (amino
acids 251-418)

-WNV TM1 (amino acids 418-442) underlined

-WNV TM2 (amino acids 443-465) underlined

-beginning yf-ns1 (amino acids 466-527)

SEQ ID NO: 1 DNA
SEQ ID NO: 2 protein
AAGGTCATCATGGGGGCGGTACTTATATGGGTTGGCATCAACACAAGAAACATGACAATG          20
  K  V  I  M  G  A  V  L  I  W  V  G  I  N  T  R  N  M  T  M TCCATGAGCATGATCTTGGTAGGAGTGATCATGATGTTTTTGTCTCTAGGAGTTGGcGCc          40
  S  M  S  M  I  L  V  G  V  I  M  M  F  L  S  L  G  V  G  A
                                                            40

GACCAGGGCTGCGCGATAAATTTCGGTaccagtctttataaaggggtttatgagcttcag        60
  D  Q  G  C  A  I  N  F  G  T  S  L  Y  K  G  V  Y  E  L  Q
  41                         49 51 actctggaactaaacatggagacactcaatatgaccatgcctctctcctgcacaaagaac        80
  T  L  E  L  N  M  E  T  L  N  M  T  M  P  L  S  C  T  K  N aacagtcatcattatataatggtgggcaatgagacaggactagaactgaccttgaccaac       100
  N  S  H  H  Y  I  M  V  G  N  E  T  G  L  E  L  T  L  T  N acgagcattattaatcacaaatttgcaatctgtctgatgcccacaaaaagaacctctat       120
  T  S  I  I  N  H  K  F  C  N  L  S  D  A  H  K  K  N  L  Y gaccacgctcttatgagcataatctcaactttccacttgtccatccccaacttcaatcag      140
  D  H  A  L  M  S  I  I  S  T  F  H  L  S  I  P  N  F  N  Q tatgaggcaatgagctgcgattttaatgggggaaagattagtgtgcagtacaacctgagt      160
  Y  E  A  M  S  C  D  F  N  G  G  K  I  S  V  Q  Y  N  L  S cacagctatgctggggatgcagccaaccattgtggtactgttgcaaatggtgtgttacag      180
  H  S  Y  A  G  D  A  A  N  H  C  G  T  V  A  N  G  V  L  Q acttttatgaggatggcttggggtgggagctacattgctcttgactcaggcTgtggcaac     200
  T  F  M  R  M  A  W  G  G  S  Y  I  A  L  D  S  G  C  G  N
                                                     R207C tgggactgtattatgactagttatcaatatctgataatccaaatacaacctgggaagat      220
  W  D  C  I  M  T  S  Y  Q  Y  L  I  I  Q  N  T  T  W  E  D cactgccaattctcgagaccatctcccatcggttatctcgggctcctctcacaaaggact     240
  H  C  Q  F  S  R  P  S  P  I  G  Y  L  G  L  S  Q  R  T agagatatttatattagtgcAAGATTGCTAGGCACATTCACATGGACACTGTCAGATTCT      260
  R  D  I  Y  I  S  A  R  L  L  G  T  F  T  W  T  L  S  D  S
                      R256A
                      247        250

GAAGGTAAAGACACACCAGGGGGATATTGTCTGACCAGGTGGATGCTAATTGAGGCTGAA      280
  E  G  K  D  T  P  G  G  Y  C  L  T  R  W  M  L  I  E  A  E

CTAAAATGCTTCGGGAACACAGCTGTGGCAAAATGTAATGAGAAGCATGATGAGGAATTT      300
  L  K  C  E  G  N  T  A  V  A  K  C  N  E  K  H  D  E  E  F
```

-continued

| SEQUENCES DEPICTED IN THE APPLICATION |
| --- |

```
TGTGACATGCTGAGGCTGTTTGACTTCAACAAACAAGCCATTCAAAGGTTGAAAGCTccA          320
 C   D   M   L   R   L   F   D   F   N   K   Q   A   I   Q   R   L   K   A   P 320
                                                                         E329P

GCACAAATGAGCATTCAGTTGATCAACAAAGCAGTAAATGCTTTGATAAATGACCAACTT          340
 A   Q   M   S   I   Q   L   I   N   K   A   V   N   A   L   I   N   D   Q   L

ATAATGAAGAACCATCTACGGGACATCATGtGtATTCCATACTGTAATTACAGCAAGTAT          360
 I   M   K   N   H   L   R   D   I   M   C   I   P   Y   C   N   Y   S   K   Y
                                    G360C

TGGTACCTCAACCACACAACTACTGGGAGAACATCACTGCCCAAATGTTGGCTTGTATCA          380
 W   Y   L   N   H   T   T   T   G   R   T   S   L   P   K   C   W   L   V   S

AATGGTTCATACTTGAACGAGACCCACTTTTCTGATGATATTGAACAACAAGCTGACAAT          400
 N   G   S   Y   L   N   E   T   H   F   S   D   D   I   E   Q   Q   A   D   N

ATGATCACTGAGATGTTACAGAAGGAGTATATGGAGAGGCAGGGGAAGACACCAGGAGGG          420
 M   I   T   E   M   L   Q   K   E   Y   M   E   R   Q   G   K   T   P   G   G
                                                                    418 419

ATGTCCTGGATCACACAGGGACTTCTGGGAGCTCTTCTGTTGTGGATGGGAATCAATGCC          440
 M   S   W   I   T   Q   G   L   L   G   A   L   L   L   W   M   G   I   N   A

CGTGACAGGTCAATTGCTATGACGTTTCTTGCGGTTGGAGGAGTTTTGCTCTTCCTTTCG          460
 R   D   R   S   I   A   M   T   F   L   A   V   G   G   V   L   L   F   L   S

GTCAACGTCCATGCTGATCAAGGATGCGCCATCAACTTTGGCAAGAGAGAGCTCAAGTGC          480
 V   N   V   H   A   D   Q   G   C   A   I   N   F   G   K   R   E   L   K   C
         465  466                        474 475

GGAGATGGTATCTTCATATTTAGAGACTCTGATGACTGGCTGAACAAGTACTCATACTAT          500
 G   D   G   I   F   I   F   R   D   S   D   D   W   L   N   K   Y   S   Y   Y

CCAGAAGATCCTGTGAAGCTTGCATCAATAGTGAAAGCCTCTTTTGAAGAAGGGAAGTGT          520
 P   E   D   P   V   K   L   A   S   I   V   K   A   S   F   E   E   G   K   C

GGCCTAAATTCAGTTGACTCC                                                527
 G   L   N   S   V   D   S
                 527
``` construct#2: PLLAV-YFV17D-LASV-GP CCS
signal peptide deleted, transmembrane domain gp2 deleted, cleavage site
restored(R246R) aND MutatIoNS R207C, E329P aND G360C)

-End YFE (amino acids 1-40)

-first 27 nucleotides ns1 (9 aminoacids) (amino acids 41-49

-lasv-gp1 [without signal peptide and mutation tgt(r207c)] (amino acids
50 to 250)

-cleavage site restored agaagattgcta (r256r) [SEQ ID NO: 17]

-lasv-gp2 [without tm and mutations cca(e329p), tgt(g360c)] (amino
acids 251 to 418)

-WNV-TM1 (amino acids 419-442

-WNV-TM2 (amino 462-465)

-beginning yf-ns1 (amino acids 466-527)

SEQ ID NO: 3
SEQ ID NO: 4
```
AAGGTCATCATGGGGGCGGTACTTATATGGGTTGGCATCAACACAAGAAACATGACAATG          20
 K   V   I   M   G   A   V   L   I   W   V   G   I   N   T   R   N   M   T   M

TCCATGAGCATGATCTTGGTAGGAGTGATCATGATGTTTTTGTCTCTAGGAGTTGGcGCc          40
 S   M   S   M   I   L   V   G   V   I   M   M   F   L   S   L   G   V   G   A
                                                                     40
```

| SEQUENCES DEPICTED IN THE APPLICATION | |
| --- | --- |

```
GACCAGGGCTGCGCGATAAATTTCGGTaccagtctttataaaggggtttatgagcttcag          60
  D  Q  G  C  A  I  N  F  G  T  S  L  Y  K  G  V  Y  E  L  Q
 41                            49 50 actctggaactaaacatggagacactcaatatgaccatgcctctctcctgcacaaagaac        80
  T  L  E  L  N  M  E  T  L  N  M  T  M  P  L  S  C  T  K  N aacagtcatcattatataatggtgggcaatgagacaggactagaactgaccttgaccaac      100
  N  S  H  H  Y  I  M  V  G  N  E  T  G  L  E  L  T  L  T  N acgagcattattaatcacaaattttgcaatctgtctgatgcccacaaaaagaacctctat      120
  T  S  I  I  N  H  K  F  C  N  L  S  D  A  H  K  K  N  L  Y gaccacgctcttatgagcataatctcaactttccacttgtccatccccaacttcaatcag      140
  D  H  A  L  M  S  I  I  S  T  F  H  L  S  I  P  N  F  N  Q tatgaggcaatgagctgcgatttttaatgggggaaagattagtgtgcagtacaacctgagt    160
  Y  E  A  M  S  C  D  F  N  G  G  K  I  S  V  Q  Y  N  L  S cacagctatgctggggatgcagccaaccattgtggtactgttgcaaatggtgtgttacag    180
  H  S  Y  A  G  D  A  A  N  H  C  G  T  V  A  N  G  V  L  Q acttttatgaggatggcttggggtgggagctacattgctcttgactcaggcTgtggcaac    200
  T  F  M  R  M  A  W  G  G  S  Y  I  A  L  D  S  G  C  G  N tgggactgtattatgactagttatcaatatctgataatccaaaatacaacctgggaagat    220
  W  D  C  I  M  T  S  Y  Q  Y  L  I  I  Q  N  T  T  W  E  D cactgccaattctcgagaccatctcccatcggttatctcgggctcctctcacaaaggact    240
  H  C  Q  F  S  R  P  S  P  I  G  Y  L  G  L  L  S  Q  R  T agagatatttatattagtagAAGATTGCTAGGCACATTCACATGGACACTGTCAGATTCT    260
  R  D  I  Y  I  S  R  R  L  L  G  T  F  T  W  T  L  S  D  S
                      R256
                      247       250

GAAGGTAAAGACACACCAGGGGGATATTGTCTGACCAGGTGGATGCTAATTGAGGCTGAA    280
  E  G  K  D  T  P  G  G  Y  C  L  T  R  W  M  L  I  E  A  E

CTAAAATGCTTCGGGAACACAGCTGTGGCAAAATGTAATGAGAAGCATGATGAGGAATTT    300
  L  K  C  F  G  N  T  A  V  A  K  C  N  E  K  H  D  E  E  F

TGTGACATGCTGAGGCTGTTTGACTTCAACAAACAAGCCATTCAAAGGTTGAAAGCTccA    320
  C  D  M  L  R  L  F  D  F  N  K  Q  A  I  Q  R  L  K  A  P

GCACAAATGAGCATTCAGTTGATCAACAAAGCAGTAAATGCTTTGATAAATGACCAACTT    340
  A  Q  M  S  I  Q  L  I  N  K  A  V  N  A  L  I  N  D  Q  L

ATAAATGAAGAACCATCTACGGGACATCATGtGtATTCCATACTGTAATTACAGCAAGTAT    360
  I  M  K  N  H  L  R  D  I  M  C  I  P  Y  C  N  Y  S  K  Y

TGGTACCTCAACCACACAACTACTGGGAGAACATCACTGCCCAAATGTTGGCTTGTATCA    380
  W  Y  L  N  H  T  T  T  G  R  T  S  L  P  K  C  W  L  V  S

AATGGTTCATACTTGAACGAGACCCACTTTTCTGATGATATTGAACAACAAGCTGACAAT    400
  N  G  S  Y  L  N  E  T  H  F  S  D  D  I  E  Q  Q  A  D  N

ATGATCACTGAGATGTTACAGAAGGAGTATATGGAGAGGCAGGGGAAGACACCAGGAGGG    420
  M  I  T  E  M  L  Q  K  E  Y  M  E  R  Q  G  K  T  P  G  G

ATGTCCTGGATCACACAGGGACTTCTGGGAGCTCTTCTGTTGTGGATGGGAATCAATGCC    440
  M  S  W  I  T  Q  G  L  L  G  A  L  L  L  W  M  G  I  N  A

CGTGACAGGTCAATTGCTATGACGTTTCTTGCGGTTGGAGGAGTTTTGCTCTTCCTTTCG    460
  R  D  R  S  I  A  M  T  F  L  A  V  G  G  V  L  L  F  L  S

GTCAACGTCCATGCTGATCAAGGATGCGCCATCAACTTTGGCAAGAGAGAGCTCAAGTGC    480
  V  N  V  H  A  D  Q  G  C  A  I  N  F  G  K  R  E  L  K  C

GGAGATGGTATCTTCATATTTAGAGACTCTGATGACTGGCTGAACAAGTACTCATACTAT    500
  G  D  G  I  F  I  F  R  D  S  D  D  W  L  N  K  Y  S  Y  Y

CCAGAAGATCCTGTGAAGCTTGCATCAATAGTGAAAGCCTCTTTTGAAGAAGGGAAGTGT    520
  P  E  D  P  V  K  L  A  S  I  V  K  A  S  F  E  E  G  K  C
```

-continued

| SEQUENCES DEPICTED IN THE APPLICATION |
|---|

GGCCTAAATTCAGTTGACTCC                                                             527
  G   L   N   S   V   D   S

Nucleotide sequence and amino acid sequence of the deleted signal
peptide(SSP)
SEQ ID NO: 5
SEQ ID NO: 6
atgggacaaatagtgacattcttccaggaagtgcctcatgtaatagaagaggtgatgaac                 20
 M  G  Q  I  V  T  F  F  Q  E  V  P  H  V  I  E  E  V  M  N attgttctcattgcactgtctgtactagcagtgctgaaaggtctgtacaattttgcaacg                 40
 I  V  L  I  A  L  S  V  L  A  V  L  K  G  L  Y  N  F  A  T tgtggccttgttggtttggtcactttcctcctgttgtgtggtaggtcttgcaca                       58
 C  G  L  V  G  L  V  T  F  L  L  L  C  G  R  S  C  T Nucleotide and amino acid sequence of the deleted LASV-GP2
transmembrane domain and cytoplasmic tail:
SEQ ID NO: 7
SEQ ID NO: 8
TTGGGTCTAGTTGACCTCTTTGTGTTCAGCACAAGTTTCTATCTTATTAGCATCTTCCTT                 20
 L  G  L  V  D  L  F  V  F  S  T  S  F  Y  L  I  S  I  F  L CACCTAGTCAAAATACCAACTCATAGGCATATTGTAGGCAAGTCGTGTCCCAAACCTCAC                 40
 H  L  V  K  I  P  T  H  R  H  I  V  G  K  S  C  P  K  P  H AGATTGAATCATATGGGCATTTGTTCCTGTGGACTCTACAAACAGCCTGGTGTGCCTGTG                 60
 R  L  N  H  M  G  I  C  S  C  G  L  Y  K  Q  P  G  V  P  V AAATGGAAGAGA                                                                  64
 K  W  K  R Lassa Josiah strain G protein sequence SEQ ID NO: 9
(amino acids 1-58: signal sequence
(amino acids 59-259: GP1 domain)
(amino acids 260-437: GP2 domain)
(amino acids 438-481: transmembrane domain and cytoplasmic tail)
MGQIVTFFQE VPHVIEEVMN IVLIALSVLA VLKGLYNFAT CGLVGLVTFL                      50

LLCGRSCTTS LYKGVYELQT LELNMETLNM TMPLSCTKNN SHHYIMVGNE                      100
      58

TGLELTLTNT SIINHKFCNL SDAHKKNLYD HALMSIISTF HLSIPNFNQY                        150

EAMSCDFNGG KISVQYNLSH SYAGDAANHC GTVANGVLQT FMRMAWGGSY                        200

IALDSGRGNW DCIMTSYQYL IIQNTTWEDH CQFSRPSPIG YLGLLSQRTR                        250

DIYISRRLLG TFTWTLSDSE GKDTPGGYCL TRWMLIEAEL KCFGNTAVAK                        300
      259

CNEKHDEEFC DMLRLFDFNK QAIQRLKAEA QMSIQLINKA VNALINDQLI                        350

MKNHLRDIMG IPYCNYSKYW YLNHTTTGRT SLPKCWLVSN GSYLNETHFS                        400

DDIEQQADNM ITEMLQKEYM ERQGKTPLGL VDLFVFSTSF YLISIFLHLV                     450
          437

KIPTHRHIVG KSCPKPHRLN HMGICSCGLY KQPGVPVKWK R                            481

NS1 signal sequence [SEQ ID NO: 10]
DQGCAINFG

Junction YFV NS1-Lassa GP1 domain [SEQ ID NO: 11]
AINFG TSLYK

Junction Lassa GP2 domain-WNV TM1 domain [SEQ ID NO: 12]
QGKTP GGMSW

Junction WNV TM2 domain-YFV NS1 [SEQ ID NO: 13]
VNVHA DQGCA

-continued

SEQUENCES DEPICTED IN THE APPLICATION

WNV TM1 sequence [SEQ ID NO: 14]
GGMSWITQGLLGALLLWMGINARD

WNV TM2 sequence [SEQ ID NO: 15]
RSIAMTFLAVGGVLLFLSVNVHA

The invention claimed is:

1. A polynucleotide comprising a sequence of a live, infectious, attenuated Flavivirus, the polynucleotide comprising:

a nucleotide sequence encoding at least a part of an arenavirus glycoprotein, the arenavirus glycoprotein comprising a GP1 domain and a GP2 domain, the arenavirus glycoprotein lacking an N terminal signal peptide and a GP2 transmembrane domain, wherein:

the nucleotide sequence is located at an intergenic region between an E gene of the Flavivirus and an NS1 gene of the Flavivirus, the E gene encoding an E protein, the NS1 gene encoding an NS1 protein, the NS1 protein comprising a signal peptide, such that a chimeric virus is expressed; and the nucleotide sequence is translatable such that the nucleotide sequence encodes a chimeric viral peptide, the chimeric viral peptide comprising:

(a) a further signal peptide, positioned C terminally of the E protein, wherein the further signal peptide has the same sequence as the signal peptide of the NS1 protein;

(b) the arenavirus glycoprotein, positioned C terminally of the further signal peptide; and (c) a TM1 and a TM2 domain of a further flaviviral E protein, positioned C terminally of the arenavirus glycoprotein; and the chimeric viral peptide is positioned N terminally of the NS1 protein of the Flavivirus.

2. The polynucleotide according to claim 1, wherein the Flavivirus is Yellow Fever virus.

3. The polynucleotide according to claim 2, wherein the Yellow Fever virus is the YF17D strain.

4. The polynucleotide according to claim 1, wherein the arenavirus glycoprotein is a Mammarena virus glycoprotein.

5. The polynucleotide according to claim 1, wherein the arenavirus glycoprotein is a Lassa virus glycoprotein.

6. The polynucleotide according to claim 1, wherein the sequence of the chimeric viral peptide comprises the amino acid sequence set forth in SEQ ID NO:2 or SEQ ID NO:4.

7. The polynucleotide according to claim 1, wherein the arenavirus glycoprotein comprises a R207C stabilizing mutation, a G360C stabilizing mutation, and an E329P stabilizing mutation.

8. The polynucleotide according to claim 1, wherein the arenavirus glycoprotein comprises a R246A proteolytic cleavage site.

9. The polynucleotide according to claim 1, wherein the further signal peptide comprises the sequence set forth by SEQ ID NO:10.

10. The polynucleotide according to claim 1, wherein the chimeric viral peptide further comprises:

the TM1 domain having the sequence set forth in SEQ ID NO:14; or the TM2 domain having the sequence set forth in SEQ ID NO:15.

11. The polynucleotide according to claim 1, further comprising a junction sequence, wherein the junction sequence is selected from the group consisting of:

the junction sequence set forth in SEQ ID NO:11, positioned between the further signal peptide sequence and the GP1 domain;

the junction sequence set forth in SEQ ID NO:12, positioned between the GP2 domain and the TM1 domain; and the junction sequence set forth in SEQ ID NO:13, positioned between the TM2 domain and the NS1 protein.

12. The polynucleotide according to claim 1, wherein the nucleotide sequence comprises:

a nucleotide sequence that is 95% identical to the nucleotide sequence set forth in SEQ ID NO:1, or a nucleotide sequence that is 95% identical to the nucleotide sequence set forth in SEQ ID NO: 3.

13. The polynucleotide according to claim 12, wherein the nucleotide sequence further comprises portions of the nucleotide sequence that encode the peptide sequences set forth in SEQ ID NO:11, SEQ ID NO:12, and SEQ ID NO:13.

14. A pharmaceutical composition comprising a polynucleotide according to claim 1 and at least one pharmaceutically acceptable carrier, diluent, or excipient.

15. A method of vaccinating an individual against an arenavirus infection, the method comprising administering to the individual the polynucleotide according to claim 1.

16. A chimeric, live, infectious, attenuated Flavivirus comprising:

an E protein;

an NS1 protein comprising a signal peptide; and a chimeric protein comprising:

at least a part of an arenavirus Glycoprotein, the arenavirus glycoprotein comprising a GP1 domain and a GP2 domain, wherein the arenavirus glycoprotein lacks an N terminal signal peptide and a GP2 transmembrane domain, and the arenavirus glycoprotein is located between the E protein and the NS1 protein;

a further signal peptide, positioned C terminally of the E protein, wherein the further signal peptide has the same sequence as the signal peptide of the NS1 protein, and wherein the arenavirus glycoprotein is positioned C terminally of the further signal peptide; and a TM1 domain and a TM2 domain of a further Flaviviral E protein, positioned C terminally of the arenavirus glycoprotein, wherein the chimeric protein is positioned N terminally of the NS1 protein.

17. The chimeric, live, infectious, attenuated Flavivirus according to claim 16, wherein the Flavivirus is Yellow Fever Virus.

18. The chimeric, live, infectious, attenuated Flavivirus according to claim 16, wherein the arenavirus glycoprotein is Lassa virus glycoprotein.

19. A pharmaceutical composition comprising a chimeric, live, infectious, attenuated Flavivirus according to claim 16 and at least one pharmaceutically acceptable carrier, diluent, or excipient.

20. A method of vaccinating an individual against an arenavirus infection, the method comprising administering to the individual the chimeric, live, infectious, attenuated Flavivirus according to claim 16.

* * * * *

SEQUENCE LISTING

<160> NUMBER OF SEQ ID NOS: 17

<210> SEQ ID NO 1
<211> LENGTH: 1581
<212> TYPE: DNA
<213> ORGANISM: Artificial Sequence
<220> FEATURE:
<223> OTHER INFORMATION: YFV Lassa chimer
<220> FEATURE:
<221> NAME/KEY: CDS
<222> LOCATION: (1)..(1581)

<400> SEQUENCE: 1

```
aag gtc atc atg ggg gcg gta ctt ata tgg gtt ggc atc aac aca aga      48
Lys Val Ile Met Gly Ala Val Leu Ile Trp Val Gly Ile Asn Thr Arg
1               5                   10                  15 aac atg aca atg tcc atg agc atg atc ttg gta gga gtg atc atg atg      96
Asn Met Thr Met Ser Met Ser Met Ile Leu Val Gly Val Ile Met Met
            20                  25                  30 ttt ttg tct cta gga gtt ggc gcc gac cag ggc tgc gcg ata aat ttc     144
Phe Leu Ser Leu Gly Val Gly Ala Asp Gln Gly Cys Ala Ile Asn Phe
        35                  40                  45 ggt acc agt ctt tat aaa ggg gtt tat gag ctt cag act ctg gaa cta     192
Gly Thr Ser Leu Tyr Lys Gly Val Tyr Glu Leu Gln Thr Leu Glu Leu
    50                  55                  60 aac atg gag aca ctc aat atg acc atg cct ctc tcc tgc aca aag aac     240
Asn Met Glu Thr Leu Asn Met Thr Met Pro Leu Ser Cys Thr Lys Asn
65                  70                  75                  80 aac agt cat cat tat ata atg gtg ggc aat gag aca gga cta gaa ctg     288
Asn Ser His His Tyr Ile Met Val Gly Asn Glu Thr Gly Leu Glu Leu
                85                  90                  95 acc ttg acc aac acg agc att att aat cac aaa ttt tgc aat ctg tct     336
Thr Leu Thr Asn Thr Ser Ile Ile Asn His Lys Phe Cys Asn Leu Ser
            100                 105                 110 gat gcc cac aaa aag aac ctc tat gac cac gct ctt atg agc ata atc     384
Asp Ala His Lys Lys Asn Leu Tyr Asp His Ala Leu Met Ser Ile Ile
        115                 120                 125 tca act ttc cac ttg tcc atc ccc aac ttc aat cag tat gag gca atg     432
Ser Thr Phe His Leu Ser Ile Pro Asn Phe Asn Gln Tyr Glu Ala Met
    130                 135                 140 agc tgc gat ttt aat ggg gga aag att agt gtg cag tac aac ctg agt     480
Ser Cys Asp Phe Asn Gly Gly Lys Ile Ser Val Gln Tyr Asn Leu Ser
145                 150                 155                 160 cac agc tat gct ggg gat gca gcc aac cat tgt ggt act gtt gca aat     528
His Ser Tyr Ala Gly Asp Ala Ala Asn His Cys Gly Thr Val Ala Asn
                165                 170                 175 ggt gtg tta cag act ttt atg agg atg gct tgg ggt ggg agc tac att     576
Gly Val Leu Gln Thr Phe Met Arg Met Ala Trp Gly Gly Ser Tyr Ile
            180                 185                 190 gct ctt gac tca ggc tgt ggc aac tgg gac tgt att atg act agt tat     624
Ala Leu Asp Ser Gly Cys Gly Asn Trp Asp Cys Ile Met Thr Ser Tyr
        195                 200                 205
```

```
caa tat ctg ata atc caa aat aca acc tgg gaa gat cac tgc caa ttc    672
Gln Tyr Leu Ile Ile Gln Asn Thr Thr Trp Glu Asp His Cys Gln Phe
    210             215                 220 tcg aga cca tct ccc atc ggt tat ctc ggg ctc ctc tca caa agg act    720
Ser Arg Pro Ser Pro Ile Gly Tyr Leu Gly Leu Leu Ser Gln Arg Thr
225             230                 235                 240 aga gat att tat att agt gca aga ttg cta ggc aca ttc aca tgg aca    768
Arg Asp Ile Tyr Ile Ser Ala Arg Leu Leu Gly Thr Phe Thr Trp Thr
                245                 250                 255 ctg tca gat tct gaa ggt aaa gac aca cca ggg gga tat tgt ctg acc    816
Leu Ser Asp Ser Glu Gly Lys Asp Thr Pro Gly Gly Tyr Cys Leu Thr
                260                 265                 270 agg tgg atg cta att gag gct gaa cta aaa tgc ttc ggg aac aca gct    864
Arg Trp Met Leu Ile Glu Ala Glu Leu Lys Cys Phe Gly Asn Thr Ala
            275                 280                 285 gtg gca aaa tgt aat gag aag cat gat gag gaa ttt tgt gac atg ctg    912
Val Ala Lys Cys Asn Glu Lys His Asp Glu Glu Phe Cys Asp Met Leu
        290                 295                 300 agg ctg ttt gac ttc aac aaa caa gcc att caa agg ttg aaa gct cca    960
Arg Leu Phe Asp Phe Asn Lys Gln Ala Ile Gln Arg Leu Lys Ala Pro
305                 310                 315                 320 gca caa atg agc att cag ttg atc aac aaa gca gta aat gct ttg ata   1008
Ala Gln Met Ser Ile Gln Leu Ile Asn Lys Ala Val Asn Ala Leu Ile
                325                 330                 335 aat gac caa ctt ata atg aag aac cat cta cgg gac atc atg tgt att   1056
Asn Asp Gln Leu Ile Met Lys Asn His Leu Arg Asp Ile Met Cys Ile
                340                 345                 350 cca tac tgt aat tac agc aag tat tgg tac ctc aac cac aca act act   1104
Pro Tyr Cys Asn Tyr Ser Lys Tyr Trp Tyr Leu Asn His Thr Thr Thr
            355                 360                 365 ggg aga aca tca ctg ccc aaa tgt tgg ctt gta tca aat ggt tca tac   1152
Gly Arg Thr Ser Leu Pro Lys Cys Trp Leu Val Ser Asn Gly Ser Tyr
        370                 375                 380 ttg aac gag acc cac ttt tct gat gat att gaa caa caa gct gac aat   1200
Leu Asn Glu Thr His Phe Ser Asp Asp Ile Glu Gln Gln Ala Asp Asn
385                 390                 395                 400 atg atc act gag atg tta cag aag gag tat atg gag agg cag ggg aag   1248
Met Ile Thr Glu Met Leu Gln Lys Glu Tyr Met Glu Arg Gln Gly Lys
                405                 410                 415 aca cca gga ggg atg tcc tgg atc aca cag gga ctt ctg gga gct ctt   1296
Thr Pro Gly Gly Met Ser Trp Ile Thr Gln Gly Leu Leu Gly Ala Leu
            420                 425                 430 ctg ttg tgg atg gga atc aat gcc cgt gac agg tca att gct atg acg   1344
Leu Leu Trp Met Gly Ile Asn Ala Arg Asp Arg Ser Ile Ala Met Thr
            435                 440                 445 ttt ctt gcg gtt gga gga gtt ttg ctc ttc ctt tcg gtc aac gtc cat   1392
Phe Leu Ala Val Gly Gly Val Leu Leu Phe Leu Ser Val Asn Val His
        450                 455                 460 gct gat caa gga tgc gcc atc aac ttt ggc aag aga gag ctc aag tgc   1440
Ala Asp Gln Gly Cys Ala Ile Asn Phe Gly Lys Arg Glu Leu Lys Cys
465                 470                 475                 480 gga gat ggt atc ttc ata ttt aga gac tct gat gac tgg ctg aac aag   1488
Gly Asp Gly Ile Phe Ile Phe Arg Asp Ser Asp Asp Trp Leu Asn Lys
                485                 490                 495 tac tca tac tat cca gaa gat cct gtg aag ctt gca tca ata gtg aaa   1536
Tyr Ser Tyr Tyr Pro Glu Asp Pro Val Lys Leu Ala Ser Ile Val Lys
            500                 505                 510 gcc tct ttt gaa gaa ggg aag tgt ggc cta aat tca gtt gac tcc      1581
Ala Ser Phe Glu Glu Gly Lys Cys Gly Leu Asn Ser Val Asp Ser
```

-continued

```
            515                 520                 525

<210> SEQ ID NO 2
<211> LENGTH: 527
<212> TYPE: PRT
<213> ORGANISM: Artificial Sequence
<220> FEATURE:
<223> OTHER INFORMATION: Synthetic Construct

<400> SEQUENCE: 2

Lys Val Ile Met Gly Ala Val Leu Ile Trp Val Gly Ile Asn Thr Arg
1               5                   10                  15

Asn Met Thr Met Ser Met Ser Met Ile Leu Val Gly Val Ile Met Met
            20                  25                  30

Phe Leu Ser Leu Gly Val Gly Ala Asp Gln Gly Cys Ala Ile Asn Phe
        35                  40                  45

Gly Thr Ser Leu Tyr Lys Gly Val Tyr Glu Leu Gln Thr Leu Glu Leu
    50                  55                  60

Asn Met Glu Thr Leu Asn Met Thr Met Pro Leu Ser Cys Thr Lys Asn
65                  70                  75                  80

Asn Ser His His Tyr Ile Met Val Gly Asn Glu Thr Gly Leu Glu Leu
                85                  90                  95

Thr Leu Thr Asn Thr Ser Ile Ile Asn His Lys Phe Cys Asn Leu Ser
            100                 105                 110

Asp Ala His Lys Lys Asn Leu Tyr Asp His Ala Leu Met Ser Ile Ile
            115                 120                 125

Ser Thr Phe His Leu Ser Ile Pro Asn Phe Asn Gln Tyr Glu Ala Met
    130                 135                 140

Ser Cys Asp Phe Asn Gly Gly Lys Ile Ser Val Gln Tyr Asn Leu Ser
145                 150                 155                 160

His Ser Tyr Ala Gly Asp Ala Ala Asn His Cys Gly Thr Val Ala Asn
                165                 170                 175

Gly Val Leu Gln Thr Phe Met Arg Met Ala Trp Gly Gly Ser Tyr Ile
            180                 185                 190

Ala Leu Asp Ser Gly Cys Gly Asn Trp Asp Cys Ile Met Thr Ser Tyr
            195                 200                 205

Gln Tyr Leu Ile Ile Gln Asn Thr Thr Trp Glu Asp His Cys Gln Phe
    210                 215                 220

Ser Arg Pro Ser Pro Ile Gly Tyr Leu Gly Leu Leu Ser Gln Arg Thr
225                 230                 235                 240

Arg Asp Ile Tyr Ile Ser Ala Arg Leu Leu Gly Thr Phe Thr Trp Thr
                245                 250                 255

Leu Ser Asp Ser Glu Gly Lys Asp Thr Pro Gly Gly Tyr Cys Leu Thr
            260                 265                 270

Arg Trp Met Leu Ile Glu Ala Glu Leu Lys Cys Phe Gly Asn Thr Ala
            275                 280                 285

Val Ala Lys Cys Asn Glu Lys His Asp Glu Glu Phe Cys Asp Met Leu
    290                 295                 300

Arg Leu Phe Asp Phe Asn Lys Gln Ala Ile Gln Arg Leu Lys Ala Pro
305                 310                 315                 320

Ala Gln Met Ser Ile Gln Leu Ile Asn Lys Ala Val Asn Ala Leu Ile
                325                 330                 335

Asn Asp Gln Leu Ile Met Lys Asn His Leu Arg Asp Ile Met Cys Ile
            340                 345                 350

Pro Tyr Cys Asn Tyr Ser Lys Tyr Trp Tyr Leu Asn His Thr Thr Thr
```

-continued

```
         355                  360                  365
Gly Arg Thr Ser Leu Pro Lys Cys Trp Leu Val Ser Asn Gly Ser Tyr
    370                  375                  380

Leu Asn Glu Thr His Phe Ser Asp Asp Ile Glu Gln Gln Ala Asp Asn
385                  390                  395                  400

Met Ile Thr Glu Met Leu Gln Lys Glu Tyr Met Glu Arg Gln Gly Lys
                 405                  410                  415

Thr Pro Gly Gly Met Ser Trp Ile Thr Gln Gly Leu Leu Gly Ala Leu
                 420                  425                  430

Leu Leu Trp Met Gly Ile Asn Ala Arg Asp Arg Ser Ile Ala Met Thr
                 435                  440                  445

Phe Leu Ala Val Gly Gly Val Leu Leu Phe Leu Ser Val Asn Val His
    450                  455                  460

Ala Asp Gln Gly Cys Ala Ile Asn Phe Gly Lys Arg Glu Leu Lys Cys
465                  470                  475                  480

Gly Asp Gly Ile Phe Ile Phe Arg Asp Ser Asp Asp Trp Leu Asn Lys
                 485                  490                  495

Tyr Ser Tyr Tyr Pro Glu Asp Pro Val Lys Leu Ala Ser Ile Val Lys
                 500                  505                  510

Ala Ser Phe Glu Glu Gly Lys Cys Gly Leu Asn Ser Val Asp Ser
                 515                  520                  525

<210> SEQ ID NO 3
<211> LENGTH: 1581
<212> TYPE: DNA
<213> ORGANISM: Artificial Sequence
<220> FEATURE:
<223> OTHER INFORMATION: YFV Lassa Chimer
<220> FEATURE:
<221> NAME/KEY: CDS
<222> LOCATION: (1)..(1581)

<400> SEQUENCE: 3 aag gtc atc atg ggg gcg gta ctt ata tgg gtt ggc atc aac aca aga      48
Lys Val Ile Met Gly Ala Val Leu Ile Trp Val Gly Ile Asn Thr Arg
1               5                   10                  15 aac atg aca atg tcc atg agc atg atc ttg gta gga gtg atc atg atg      96
Asn Met Thr Met Ser Met Ser Met Ile Leu Val Gly Val Ile Met Met
            20                  25                  30 ttt ttg tct cta gga gtt ggc gcc gac cag ggc tgc gcg ata aat ttc     144
Phe Leu Ser Leu Gly Val Gly Ala Asp Gln Gly Cys Ala Ile Asn Phe
        35                  40                  45 ggt acc agt ctt tat aaa ggg gtt tat gag ctt cag act ctg gaa cta     192
Gly Thr Ser Leu Tyr Lys Gly Val Tyr Glu Leu Gln Thr Leu Glu Leu
    50                  55                  60 aac atg gag aca ctc aat atg acc atg cct ctc tcc tgc aca aag aac     240
Asn Met Glu Thr Leu Asn Met Thr Met Pro Leu Ser Cys Thr Lys Asn
65                  70                  75                  80 aac agt cat cat tat ata atg gtg ggc aat gag aca gga cta gaa ctg     288
Asn Ser His His Tyr Ile Met Val Gly Asn Glu Thr Gly Leu Glu Leu
                 85                  90                  95 acc ttg acc aac acg agc att att aat cac aaa ttt tgc aat ctg tct     336
Thr Leu Thr Asn Thr Ser Ile Ile Asn His Lys Phe Cys Asn Leu Ser
            100                 105                 110 gat gcc cac aaa aag aac ctc tat gac cac gct ctt atg agc ata atc     384
Asp Ala His Lys Lys Asn Leu Tyr Asp His Ala Leu Met Ser Ile Ile
        115                 120                 125 tca act ttc cac ttg tcc atc ccc aac ttc aat cag tat gag gca atg     432
Ser Thr Phe His Leu Ser Ile Pro Asn Phe Asn Gln Tyr Glu Ala Met
```

```
            130                    135                    140
agc tgc gat ttt aat ggg gga aag att agt gtg cag tac aac ctg agt        480
Ser Cys Asp Phe Asn Gly Gly Lys Ile Ser Val Gln Tyr Asn Leu Ser
145                 150                    155                    160 cac agc tat gct ggg gat gca gcc aac cat tgt ggt act gtt gca aat        528
His Ser Tyr Ala Gly Asp Ala Ala Asn His Cys Gly Thr Val Ala Asn
                    165                    170                    175 ggt gtg tta cag act ttt atg agg atg gct tgg ggt ggg agc tac att        576
Gly Val Leu Gln Thr Phe Met Arg Met Ala Trp Gly Gly Ser Tyr Ile
                180                    185                    190 gct ctt gac tca ggc tgt ggc aac tgg gac tgt att atg act agt tat        624
Ala Leu Asp Ser Gly Cys Gly Asn Trp Asp Cys Ile Met Thr Ser Tyr
                195                    200                    205 caa tat ctg ata atc caa aat aca acc tgg gaa gat cac tgc caa ttc        672
Gln Tyr Leu Ile Ile Gln Asn Thr Thr Trp Glu Asp His Cys Gln Phe
            210                    215                    220 tcg aga cca tct ccc atc ggt tat ctc ggg ctc ctc tca caa agg act        720
Ser Arg Pro Ser Pro Ile Gly Tyr Leu Gly Leu Leu Ser Gln Arg Thr
225                 230                    235                    240 aga gat att tat att agt aga aga ttg cta ggc aca ttc aca tgg aca        768
Arg Asp Ile Tyr Ile Ser Arg Arg Leu Leu Gly Thr Phe Thr Trp Thr
                    245                    250                    255 ctg tca gat tct gaa ggt aaa gac aca cca ggg gga tat tgt ctg acc        816
Leu Ser Asp Ser Glu Gly Lys Asp Thr Pro Gly Gly Tyr Cys Leu Thr
                260                    265                    270 agg tgg atg cta att gag gct gaa cta aaa tgc ttc ggg aac aca gct        864
Arg Trp Met Leu Ile Glu Ala Glu Leu Lys Cys Phe Gly Asn Thr Ala
                275                    280                    285 gtg gca aaa tgt aat gag aag cat gat gag gaa ttt tgt gac atg ctg        912
Val Ala Lys Cys Asn Glu Lys His Asp Glu Glu Phe Cys Asp Met Leu
            290                    295                    300 agg ctg ttt gac ttc aac aaa caa gcc att caa agg ttg aaa gct cca        960
Arg Leu Phe Asp Phe Asn Lys Gln Ala Ile Gln Arg Leu Lys Ala Pro
305                 310                    315                    320 gca caa atg agc att cag ttg atc aac aaa gca gta aat gct ttg ata       1008
Ala Gln Met Ser Ile Gln Leu Ile Asn Lys Ala Val Asn Ala Leu Ile
                    325                    330                    335 aat gac caa ctt ata atg aag aac cat cta cgg gac atc atg tgt att       1056
Asn Asp Gln Leu Ile Met Lys Asn His Leu Arg Asp Ile Met Cys Ile
                340                    345                    350 cca tac tgt aat tac agc aag tat tgg tac ctc aac cac aca act act       1104
Pro Tyr Cys Asn Tyr Ser Lys Tyr Trp Tyr Leu Asn His Thr Thr Thr
                355                    360                    365 ggg aga aca tca ctg ccc aaa tgt tgg ctt gta tca aat ggt tca tac       1152
Gly Arg Thr Ser Leu Pro Lys Cys Trp Leu Val Ser Asn Gly Ser Tyr
            370                    375                    380 ttg aac gag acc cac ttt tct gat gat att gaa caa caa gct gac aat       1200
Leu Asn Glu Thr His Phe Ser Asp Asp Ile Glu Gln Gln Ala Asp Asn
385                 390                    395                    400 atg atc act gag atg tta cag aag gag tat atg gag agg cag ggg aag       1248
Met Ile Thr Glu Met Leu Gln Lys Glu Tyr Met Glu Arg Gln Gly Lys
                    405                    410                    415 aca cca gga ggg atg tcc tgg atc aca cag gga ctt ctg gga gct ctt       1296
Thr Pro Gly Gly Met Ser Trp Ile Thr Gln Gly Leu Leu Gly Ala Leu
                420                    425                    430 ctg ttg tgg atg gga atc aat gcc cgt gac agg tca att gct atg acg       1344
Leu Leu Trp Met Gly Ile Asn Ala Arg Asp Arg Ser Ile Ala Met Thr
                435                    440                    445 ttt ctt gcg gtt gga gga gtt ttg ctc ttc ctt tcg gtc aac gtc cat       1392
```

-continued

```
Phe Leu Ala Val Gly Gly Val Leu Leu Phe Leu Ser Val Asn Val His
    450             455             460 gct gat caa gga tgc gcc atc aac ttt ggc aag aga gag ctc aag tgc      1440
Ala Asp Gln Gly Cys Ala Ile Asn Phe Gly Lys Arg Glu Leu Lys Cys
465             470             475             480 gga gat ggt atc ttc ata ttt aga gac tct gat gac tgg ctg aac aag      1488
Gly Asp Gly Ile Phe Ile Phe Arg Asp Ser Asp Asp Trp Leu Asn Lys
            485             490             495 tac tca tac tat cca gaa gat cct gtg aag ctt gca tca ata gtg aaa      1536
Tyr Ser Tyr Tyr Pro Glu Asp Pro Val Lys Leu Ala Ser Ile Val Lys
            500             505             510 gcc tct ttt gaa gaa ggg aag tgt ggc cta aat tca gtt gac tcc          1581
Ala Ser Phe Glu Glu Gly Lys Cys Gly Leu Asn Ser Val Asp Ser
        515             520             525

<210> SEQ ID NO 4
<211> LENGTH: 527
<212> TYPE: PRT
<213> ORGANISM: Artificial Sequence
<220> FEATURE:
<223> OTHER INFORMATION: Synthetic Construct

<400> SEQUENCE: 4

Lys Val Ile Met Gly Ala Val Leu Ile Trp Val Gly Ile Asn Thr Arg
1               5               10              15

Asn Met Thr Met Ser Met Ser Met Ile Leu Val Gly Val Ile Met Met
            20              25              30

Phe Leu Ser Leu Gly Val Gly Ala Asp Gln Gly Cys Ala Ile Asn Phe
            35              40              45

Gly Thr Ser Leu Tyr Lys Gly Val Tyr Glu Leu Gln Thr Leu Glu Leu
        50              55              60

Asn Met Glu Thr Leu Asn Met Thr Met Pro Leu Ser Cys Thr Lys Asn
65              70              75              80

Asn Ser His His Tyr Ile Met Val Gly Asn Glu Thr Gly Leu Glu Leu
            85              90              95

Thr Leu Thr Asn Thr Ser Ile Ile Asn His Lys Phe Cys Asn Leu Ser
            100             105             110

Asp Ala His Lys Lys Asn Leu Tyr Asp His Ala Leu Met Ser Ile Ile
        115             120             125

Ser Thr Phe His Leu Ser Ile Pro Asn Phe Asn Gln Tyr Glu Ala Met
    130             135             140

Ser Cys Asp Phe Asn Gly Gly Lys Ile Ser Val Gln Tyr Asn Leu Ser
145             150             155             160

His Ser Tyr Ala Gly Asp Ala Ala Asn His Cys Gly Thr Val Ala Asn
            165             170             175

Gly Val Leu Gln Thr Phe Met Arg Met Ala Trp Gly Gly Ser Tyr Ile
            180             185             190

Ala Leu Asp Ser Gly Cys Gly Asn Trp Asp Cys Ile Met Thr Ser Tyr
        195             200             205

Gln Tyr Leu Ile Ile Gln Asn Thr Thr Trp Glu Asp His Cys Gln Phe
    210             215             220

Ser Arg Pro Ser Pro Ile Gly Tyr Leu Gly Leu Leu Ser Gln Arg Thr
225             230             235             240

Arg Asp Ile Tyr Ile Ser Arg Arg Leu Leu Gly Thr Phe Thr Trp Thr
            245             250             255

Leu Ser Asp Ser Glu Gly Lys Asp Thr Pro Gly Gly Tyr Cys Leu Thr
            260             265             270
```

-continued

```
Arg Trp Met Leu Ile Glu Ala Glu Leu Lys Cys Phe Gly Asn Thr Ala
    275                 280                 285

Val Ala Lys Cys Asn Glu Lys His Asp Glu Glu Phe Cys Asp Met Leu
    290                 295                 300

Arg Leu Phe Asp Phe Asn Lys Gln Ala Ile Gln Arg Leu Lys Ala Pro
305                 310                 315                 320

Ala Gln Met Ser Ile Gln Leu Ile Asn Lys Ala Val Asn Ala Leu Ile
                325                 330                 335

Asn Asp Gln Leu Ile Met Lys Asn His Leu Arg Asp Ile Met Cys Ile
                340                 345                 350

Pro Tyr Cys Asn Tyr Ser Lys Tyr Trp Tyr Leu Asn His Thr Thr Thr
                355                 360                 365

Gly Arg Thr Ser Leu Pro Lys Cys Trp Leu Val Ser Asn Gly Ser Tyr
    370                 375                 380

Leu Asn Glu Thr His Phe Ser Asp Asp Ile Glu Gln Gln Ala Asp Asn
385                 390                 395                 400

Met Ile Thr Glu Met Leu Gln Lys Glu Tyr Met Glu Arg Gln Gly Lys
                405                 410                 415

Thr Pro Gly Gly Met Ser Trp Ile Thr Gln Gly Leu Leu Gly Ala Leu
                420                 425                 430

Leu Leu Trp Met Gly Ile Asn Ala Arg Asp Arg Ser Ile Ala Met Thr
                435                 440                 445

Phe Leu Ala Val Gly Gly Val Leu Leu Phe Leu Ser Val Asn Val His
    450                 455                 460

Ala Asp Gln Gly Cys Ala Ile Asn Phe Gly Lys Arg Glu Leu Lys Cys
465                 470                 475                 480

Gly Asp Gly Ile Phe Ile Phe Arg Asp Ser Asp Asp Trp Leu Asn Lys
                485                 490                 495

Tyr Ser Tyr Tyr Pro Glu Asp Pro Val Lys Leu Ala Ser Ile Val Lys
                500                 505                 510

Ala Ser Phe Glu Glu Gly Lys Cys Gly Leu Asn Ser Val Asp Ser
        515                 520                 525
```

```
<210> SEQ ID NO 5
<211> LENGTH: 174
<212> TYPE: DNA
<213> ORGANISM: Lassa virus
<220> FEATURE:
<221> NAME/KEY: CDS
<222> LOCATION: (1)..(174)

<400> SEQUENCE: 5 atg gga caa ata gtg aca ttc ttc cag gaa gtg cct cat gta ata gaa        48
Met Gly Gln Ile Val Thr Phe Phe Gln Glu Val Pro His Val Ile Glu
1               5                   10                  15 gag gtg atg aac att gtt ctc att gca ctg tct gta cta gca gtg ctg        96
Glu Val Met Asn Ile Val Leu Ile Ala Leu Ser Val Leu Ala Val Leu
                20                  25                  30 aaa ggt ctg tac aat ttt gca acg tgt ggc ctt gtt ggt ttg gtc act       144
Lys Gly Leu Tyr Asn Phe Ala Thr Cys Gly Leu Val Gly Leu Val Thr
                35                  40                  45 ttc ctc ctg ttg tgt ggt agg tct tgc aca                               174
Phe Leu Leu Leu Cys Gly Arg Ser Cys Thr
        50                  55
```

```
<210> SEQ ID NO 6
<211> LENGTH: 58
```

<212> TYPE: PRT
<213> ORGANISM: Lassa virus

<400> SEQUENCE: 6

```
Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
                20                  25                  30

Lys Gly Leu Tyr Asn Phe Ala Thr Cys Gly Leu Val Gly Leu Val Thr
            35                  40                  45

Phe Leu Leu Leu Cys Gly Arg Ser Cys Thr
        50                  55
```

<210> SEQ ID NO 7
<211> LENGTH: 192
<212> TYPE: DNA
<213> ORGANISM: Lassa virus
<220> FEATURE:
<221> NAME/KEY: CDS
<222> LOCATION: (1)..(192)

<400> SEQUENCE: 7

```
ttg ggt cta gtt gac ctc ttt gtg ttc agc aca agt ttc tat ctt att      48
Leu Gly Leu Val Asp Leu Phe Val Phe Ser Thr Ser Phe Tyr Leu Ile
1               5                   10                  15 agc atc ttc ctt cac cta gtc aaa ata cca act cat agg cat att gta      96
Ser Ile Phe Leu His Leu Val Lys Ile Pro Thr His Arg His Ile Val
                20                  25                  30 ggc aag tcg tgt ccc aaa cct cac aga ttg aat cat atg ggc att tgt     144
Gly Lys Ser Cys Pro Lys Pro His Arg Leu Asn His Met Gly Ile Cys
            35                  40                  45 tcc tgt gga ctc tac aaa cag cct ggt gtg cct gtg aaa tgg aag aga     192
Ser Cys Gly Leu Tyr Lys Gln Pro Gly Val Pro Val Lys Trp Lys Arg
        50                  55                  60
```

<210> SEQ ID NO 8
<211> LENGTH: 64
<212> TYPE: PRT
<213> ORGANISM: Lassa virus

<400> SEQUENCE: 8

```
Leu Gly Leu Val Asp Leu Phe Val Phe Ser Thr Ser Phe Tyr Leu Ile
1               5                   10                  15

Ser Ile Phe Leu His Leu Val Lys Ile Pro Thr His Arg His Ile Val
                20                  25                  30

Gly Lys Ser Cys Pro Lys Pro His Arg Leu Asn His Met Gly Ile Cys
            35                  40                  45

Ser Cys Gly Leu Tyr Lys Gln Pro Gly Val Pro Val Lys Trp Lys Arg
        50                  55                  60
```

<210> SEQ ID NO 9
<211> LENGTH: 491
<212> TYPE: PRT
<213> ORGANISM: Lassa virus

<400> SEQUENCE: 9

```
Met Gly Gln Ile Val Thr Phe Phe Gln Glu Val Pro His Val Ile Glu
1               5                   10                  15

Glu Val Met Asn Ile Val Leu Ile Ala Leu Ser Val Leu Ala Val Leu
                20                  25                  30

Lys Gly Leu Tyr Asn Phe Ala Thr Cys Gly Leu Val Gly Leu Val Thr
```

-continued

```
            35                  40                  45
Phe Leu Leu Leu Cys Gly Arg Ser Cys Thr Thr Ser Leu Tyr Lys Gly
    50                  55                  60

Val Tyr Glu Leu Gln Thr Leu Glu Leu Asn Met Glu Thr Leu Asn Met
65                  70                  75                  80

Thr Met Pro Leu Ser Cys Thr Lys Asn Asn Ser His His Tyr Ile Met
                85                  90                  95

Val Gly Asn Glu Thr Gly Leu Glu Leu Thr Leu Thr Asn Thr Ser Ile
            100                 105                 110

Ile Asn His Lys Phe Cys Asn Leu Ser Asp Ala His Lys Lys Asn Leu
            115                 120                 125

Tyr Asp His Ala Leu Met Ser Ile Ile Ser Thr Phe His Leu Ser Ile
    130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
            165                 170                 175

Ala Asn His Cys Gly Thr Val Ala Asn Gly Val Leu Gln Thr Phe Met
            180                 185                 190

Arg Met Ala Trp Gly Gly Ser Tyr Ile Ala Leu Asp Ser Gly Arg Gly
    195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
            245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
            275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320

Gln Ala Ile Gln Arg Leu Lys Ala Glu Ala Gln Met Ser Ile Gln Leu
            325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
    355                 360                 365

Tyr Trp Tyr Leu Asn His Thr Thr Thr Gly Arg Thr Ser Leu Pro Lys
    370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
            405                 410                 415

Lys Glu Tyr Met Glu Arg Gln Gly Lys Thr Pro Leu Gly Leu Val Asp
            420                 425                 430

Leu Phe Val Phe Ser Thr Ser Phe Tyr Leu Ile Ser Ile Phe Leu His
    435                 440                 445

Leu Val Lys Ile Pro Thr His Arg His Ile Val Gly Lys Ser Cys Pro
    450                 455                 460
```

```
Lys Pro His Arg Leu Asn His Met Gly Ile Cys Ser Cys Gly Leu Tyr
465                 470                 475                 480

Lys Gln Pro Gly Val Pro Val Lys Trp Lys Arg
                485                 490

<210> SEQ ID NO 10
<211> LENGTH: 9
<212> TYPE: PRT
<213> ORGANISM: Yellow fever virus

<400> SEQUENCE: 10

Asp Gln Gly Cys Ala Ile Asn Phe Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Junction YFV NS1- Lassa GP1 domain

<400> SEQUENCE: 11

Ala Ile Asn Phe Gly Thr Ser Leu Tyr Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Junction Lassa GP2 domain - WNV TM1 domain

<400> SEQUENCE: 12

Gln Gly Lys Thr Pro Gly Gly Met Ser Trp
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Junction WNV TM2  domain - YFV NS1

<400> SEQUENCE: 13

Val Asn Val His Ala Asp Gln Gly Cys Ala
1               5                   10

<210> SEQ ID NO 14
<211> LENGTH: 24
<212> TYPE: PRT
<213> ORGANISM: West Nile virus

<400> SEQUENCE: 14

Gly Gly Met Ser Trp Ile Thr Gln Gly Leu Leu Gly Ala Leu Leu Leu
1               5                   10                  15

Trp Met Gly Ile Asn Ala Arg Asp
                20

<210> SEQ ID NO 15
<211> LENGTH: 23
<212> TYPE: PRT
<213> ORGANISM: West Nile virus

<400> SEQUENCE: 15
```

-continued

```
Arg Ser Ile Ala Met Thr Phe Leu Ala Val Gly Gly Val Leu Leu Phe
1               5                   10                  15

Leu Ser Val Asn Val His Ala
            20

<210> SEQ ID NO 16
<211> LENGTH: 12
<212> TYPE: DNA
<213> ORGANISM: Artificial Sequence
<220> FEATURE:
<223> OTHER INFORMATION: mutated cleavage site

<400> SEQUENCE: 16
gcaagattgc ta                                                    12

<210> SEQ ID NO 17
<211> LENGTH: 12
<212> TYPE: DNA
<213> ORGANISM: Artificial Sequence
<220> FEATURE:
<223> OTHER INFORMATION: restored cleavage site

<400> SEQUENCE: 17
agaagattgc ta                                                    12
```